(12) United States Patent
Carlson et al.

(10) Patent No.: US 8,900,310 B2
(45) Date of Patent: Dec. 2, 2014

(54) INTERBODY SPACER

(75) Inventors: Daniel A. Carlson, St. Louis Park, MN (US); Hugh D. Hestad, Edina, MN (US); Jack A. Dant, St. Paul, MN (US); Reginald J. Davis, Cockeysville, MD (US)

(73) Assignee: Zimmer Spine, Inc., Minneapolis, MN (US)

( * ) Notice: Subject to any disclaimer, the term of this patent is extended or adjusted under 35 U.S.C. 154(b) by 75 days.

(21) Appl. No.: 13/440,387

(22) Filed: Apr. 5, 2012

(65) Prior Publication Data

US 2013/0268076 A1   Oct. 10, 2013

(51) Int. Cl.
*A61F 2/44* (2006.01)

(52) U.S. Cl.
USPC ...................................... 623/17.16

(58) Field of Classification Search
CPC .............. A61F 2220/0025; A61F 2002/30364; A61F 2002/30405; A61F 2002/30616; A61F 2002/30904; A61F 2/44
USPC ............... 623/17.11–17.16; 606/60, 246–249
See application file for complete search history.

(56) References Cited

U.S. PATENT DOCUMENTS

| | | | |
|---|---|---|---|
| 5,683,394 A * | 11/1997 | Rinner ........................ | 606/86 R |
| 5,800,547 A | 9/1998 | Schaefer et al. | |
| 5,888,228 A | 3/1999 | Knothe et al. | |
| 6,090,143 A | 7/2000 | Meriwether et al. | |
| 6,102,949 A | 8/2000 | Biedermann et al. | |
| 6,179,873 B1 | 1/2001 | Zientek | |
| 6,210,442 B1 | 4/2001 | Wing et al. | |
| 6,290,724 B1 * | 9/2001 | Marino ........................ | 623/17.11 |
| 6,770,096 B2 | 8/2004 | Bolger et al. | |
| 6,824,564 B2 | 11/2004 | Crozet | |
| 7,041,135 B2 * | 5/2006 | Michelson ................. | 623/17.11 |
| 7,232,463 B2 * | 6/2007 | Falahee ....................... | 623/17.11 |
| 7,594,932 B2 | 9/2009 | Aferzon et al. | |
| 7,621,938 B2 * | 11/2009 | Molz, IV ....................... | 606/246 |
| 7,744,649 B2 * | 6/2010 | Moore ........................ | 623/17.11 |
| 7,771,475 B2 | 8/2010 | Michelson | |
| 8,100,972 B1 * | 1/2012 | Bruffey et al. .............. | 623/17.11 |
| 8,142,508 B1 * | 3/2012 | Bruffey et al. .............. | 623/17.16 |
| 8,292,958 B1 * | 10/2012 | Bruffey et al. .............. | 623/17.11 |
| 8,328,870 B2 * | 12/2012 | Patel et al. .................. | 623/17.11 |
| 8,366,774 B1 * | 2/2013 | Bruffey et al. .............. | 623/17.11 |
| 8,439,977 B2 * | 5/2013 | Kostuik et al. .............. | 623/17.16 |
| 2002/0161445 A1 * | 10/2002 | Crozet ....................... | 623/17.11 |
| 2003/0060825 A1 | 3/2003 | Alfaro et al. | |
| 2004/0153156 A1 * | 8/2004 | Cohen et al. ................ | 623/17.13 |
| 2005/0113830 A1 * | 5/2005 | Rezach et al. ................ | 606/60 |
| 2005/0159813 A1 * | 7/2005 | Molz ........................... | 623/17.11 |
| 2005/0273168 A1 * | 12/2005 | Crozet ....................... | 623/17.11 |

(Continued)

*Primary Examiner* — Ellen C Hammond
*Assistant Examiner* — Jacqueline Johanas
(74) *Attorney, Agent, or Firm* — Seager, Tufte & Wickhem, LLC

(57) ABSTRACT

An intervertebral or spinal implant having a spacer, a cage, and a locking mechanism, where the locking mechanism may be configured to facilitate a connection between the spacer and the cage. In some cases, the spacer may include a distal end wall, a proximal end wall, a first lateral wall, and a second lateral wall, where the locking mechanism may be situated at the proximal end wall adjacent a receiving opening in the proximal end wall. The implant may have one or more spikes extending from a top and/or a bottom of the spacer to facilitate stabilizing the implant between vertebrae after insertion of the implant in the spinal column.

25 Claims, 27 Drawing Sheets

(56) References Cited

U.S. PATENT DOCUMENTS

| | | | |
|---|---|---|---|
| 2005/0283236 A1* | 12/2005 | Razian | 623/17.11 |
| 2008/0027550 A1* | 1/2008 | Link et al. | 623/17.16 |
| 2008/0132949 A1* | 6/2008 | Aferzon et al. | 606/246 |
| 2008/0249625 A1* | 10/2008 | Waugh et al. | 623/17.16 |
| 2009/0164015 A1* | 6/2009 | Liu et al. | 623/17.11 |
| 2009/0265007 A1* | 10/2009 | Colleran | 623/17.16 |
| 2010/0030334 A1* | 2/2010 | Molz, IV | 623/17.11 |
| 2010/0087925 A1* | 4/2010 | Kostuik et al. | 623/17.16 |
| 2011/0166660 A1 | 7/2011 | Laurence | |
| 2011/0178599 A1* | 7/2011 | Brett | 623/17.16 |
| 2012/0095561 A1* | 4/2012 | Voisard et al. | 623/17.16 |
| 2012/0197402 A1* | 8/2012 | Blackwell et al. | 623/17.16 |
| 2012/0271423 A1* | 10/2012 | Wallenstein et al. | 623/17.16 |

* cited by examiner

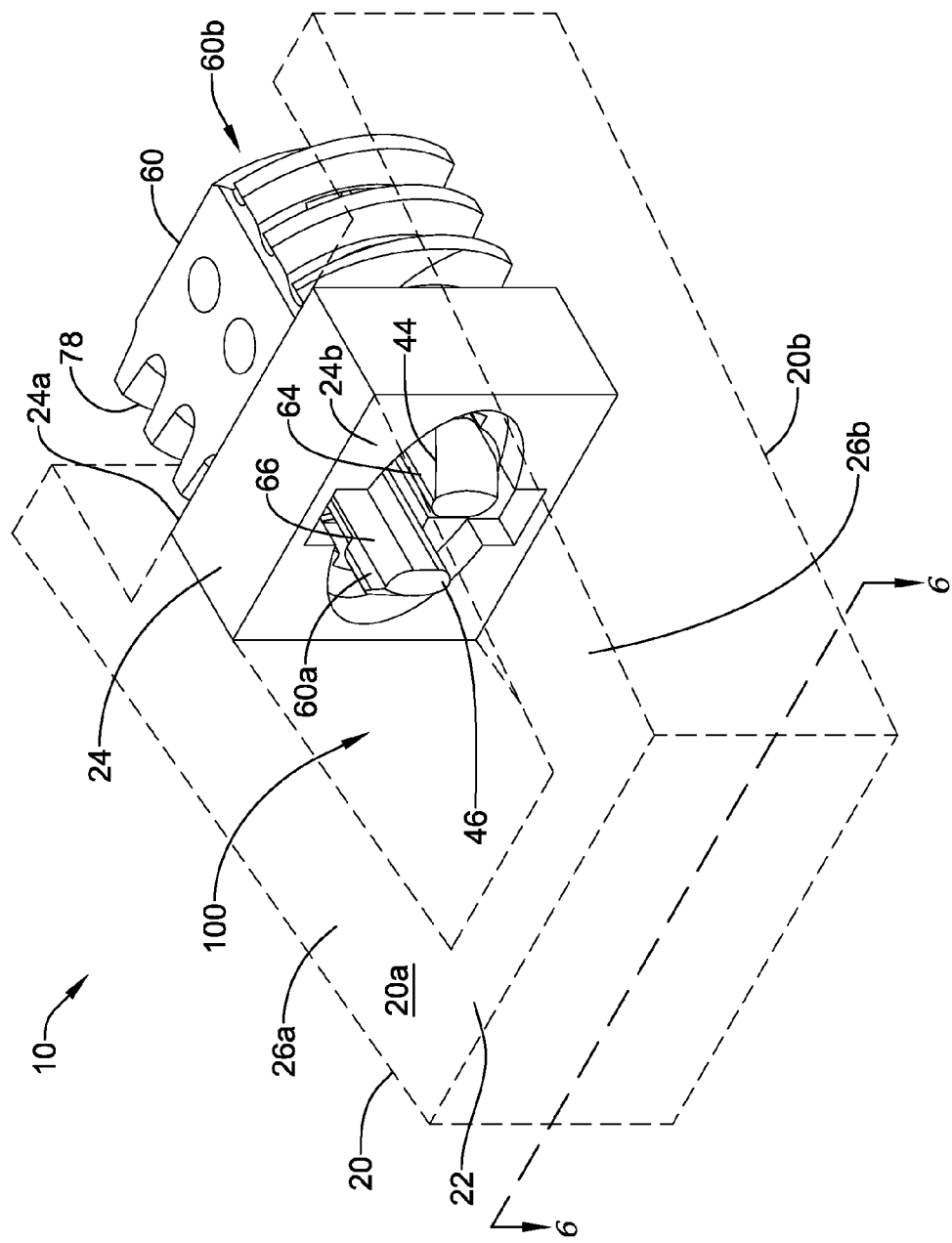

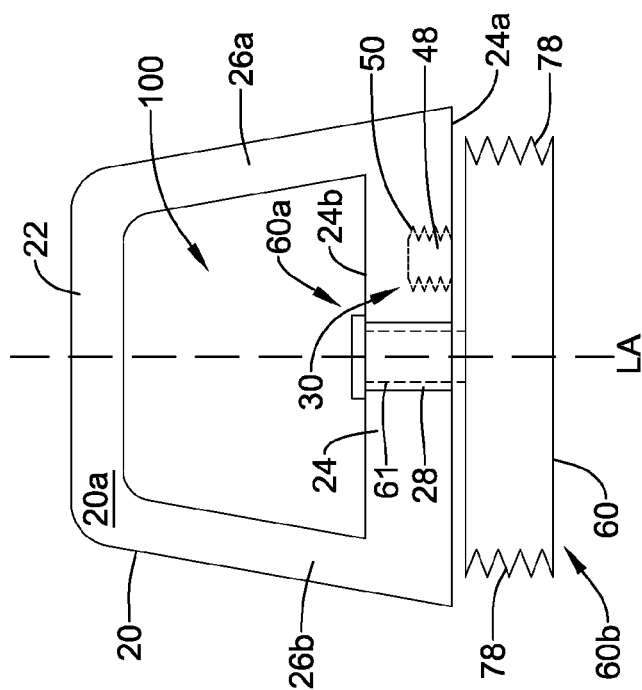
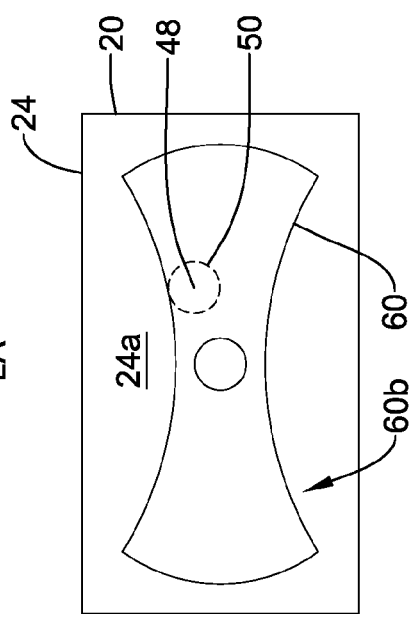

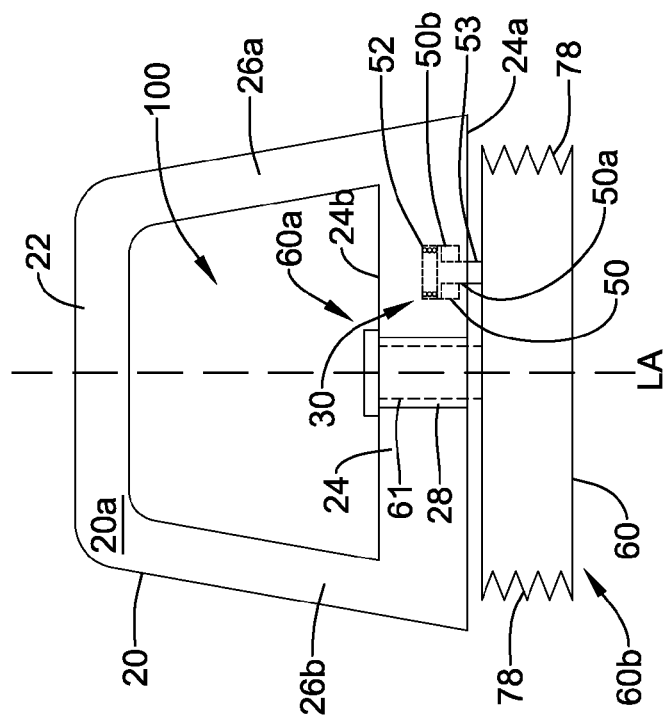
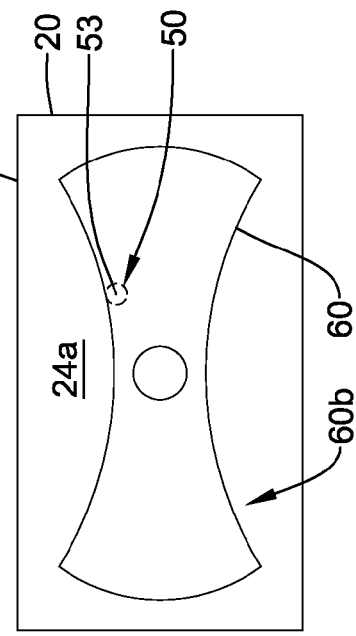
Figure 11A
Figure 11B

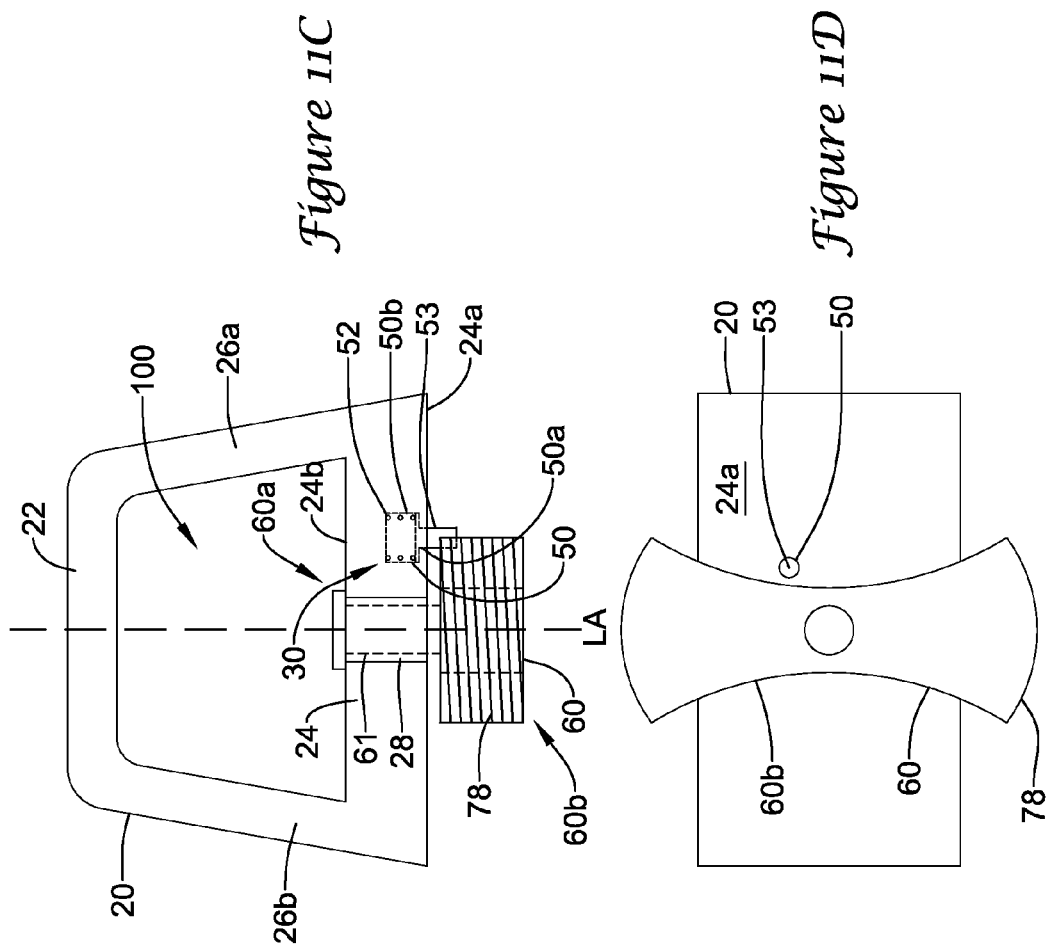

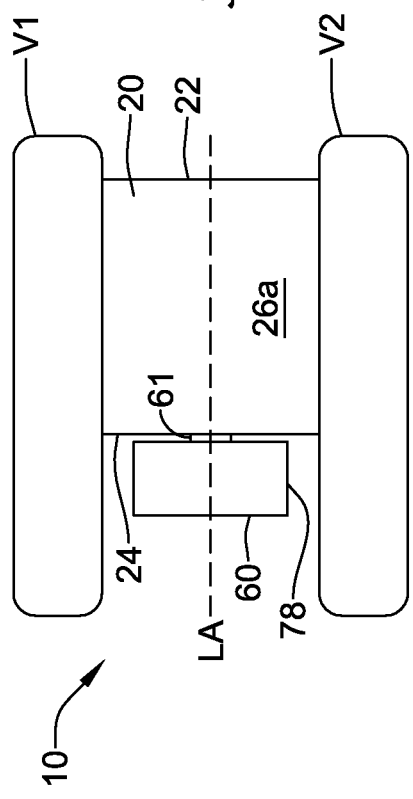
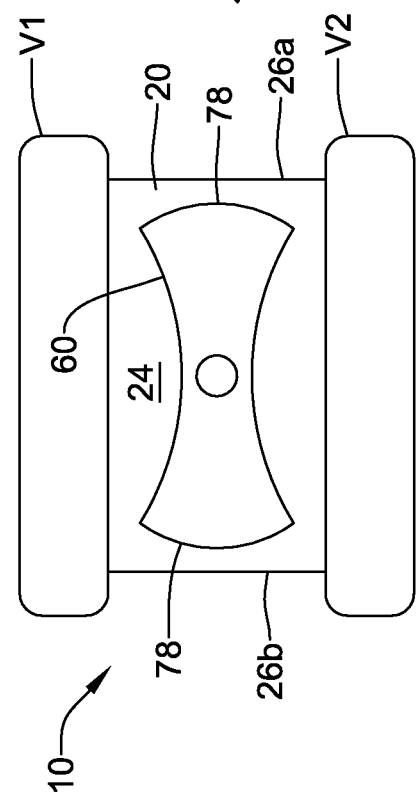

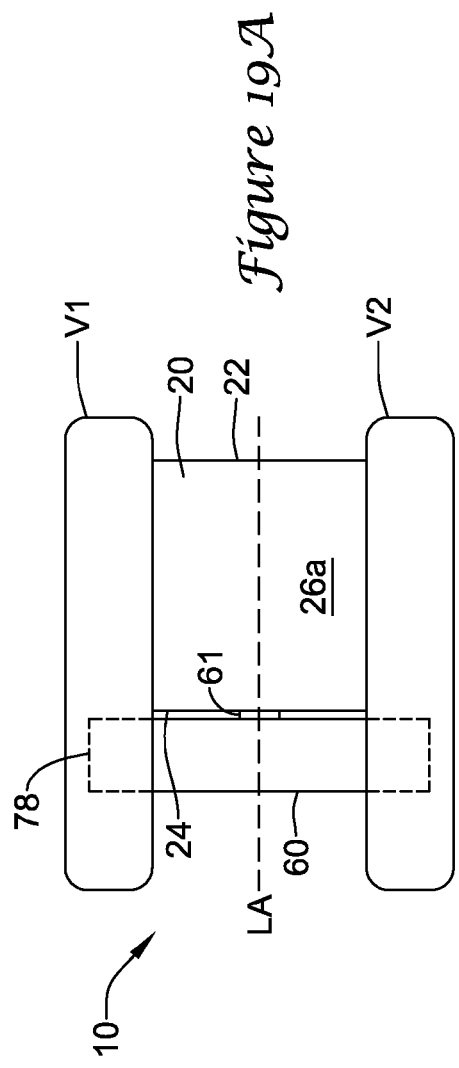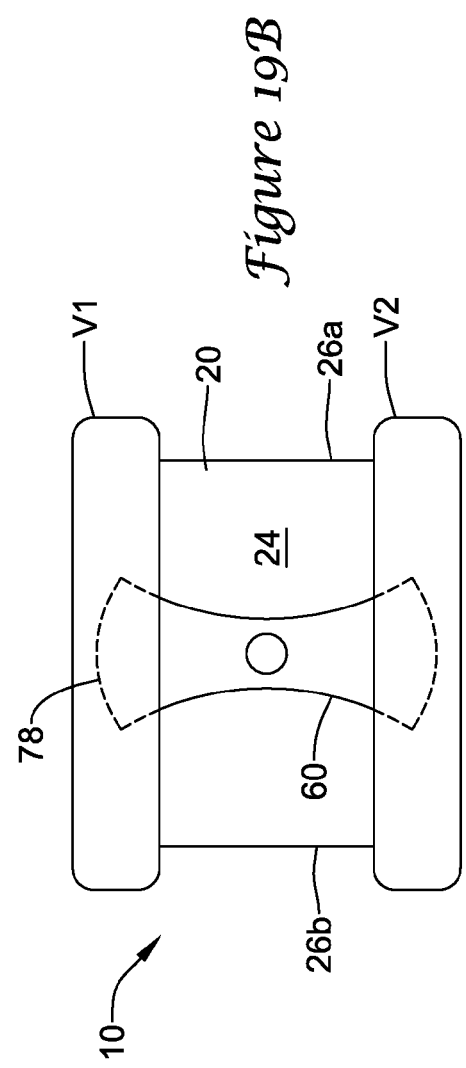

INTERBODY SPACER

TECHNICAL FIELD

The disclosure is directed to interbody spinal devices. More particularly, the disclosure is directed to devices for use in intervertebral implant procedures.

BACKGROUND

A damaged or degenerated intervertebral disc between adjacent vertebrae may prompt spinal surgery to alleviate pain or otherwise stabilize the vertebral segment. During a spinal fixation procedure, an intervertebral implant may be inserted within a space created by the removal or partial removal of an intervertebral disc between adjacent vertebrae. The intervertebral implant may maintain the proper spacing and/or lordosis between vertebrae and restore stability to the spine. Subsequent bone growth may fuse the implant to the adjacent vertebrae to provide further stabilization.

It is desirable to prevent the implant from migrating within the disc space between the adjacent vertebrae until fusion of the bones occurs. Various means of supplemental fixation have been implemented to provide initial securement of the implant to the vertebrae to resist migration. However, there is an ongoing need to provide alternative intervertebral implants and associated means of providing stabilization of the intervertebral implants between the vertebrae until fusion occurs.

SUMMARY

The disclosure is directed to several alternative or complementary designs, materials, and methods of using medical device structures and assemblies. Although it is noted that conventional intervertebral implants and similar devices exist, there exists a need for improvement on those devices.

Accordingly, one illustrative embodiment of the disclosure may include an intervertebral or spinal implant having a spacer, a cage, and a locking mechanism, where the locking mechanism may be configured to facilitate a connection between the spacer and the cage. In some cases, the spacer may include a grafting space at least partially defined by a distal end wall, a proximal end wall, a first lateral wall, and/or a second lateral wall, where the locking mechanism may be situated adjacent a receiving opening of the proximal end wall. The locking mechanism may include a first end of the cage engaging the receiving opening in the proximal end wall, a cam, a spring loaded post, a threaded post, and/or any other object configured to connect and/or maintain a connection between the cage and the spacer. In an illustrative example, the first end of the cage may include threads, and/or one or more deflection inserts that engage receiving threads and/or indentations in the proximal end wall of the spacer to create a locking connection between the cage and the spacer. In operation, the first end of the cage may be inserted into the receiving opening of the spacer and then the implant may be inserted into the spinal column, where after insertion in the spinal column, the cage may be rotated such that it engages the vertebrae of the spinal column and, optionally, facilitates the creation of a locking connection between the cage and the spacer.

In some instances, the implant may have one or more spikes extending from a top and/or a bottom of the spacer (e.g., from the top and the bottom of the distal end wall of the spacer). Illustratively, the spike(s) may be compressible to facilitate insertion of the implant into the spinal column, while being configured to engage vertebrae of the spinal column after insertion of the implant to assist in stabilizing the implant with respect to the vertebrae.

The above summary of some example aspects is not intended to describe each disclosed embodiment or every implementation of the claimed disclosure.

BRIEF DESCRIPTION OF THE DRAWINGS

The disclosure may be more completely understood in consideration of the following detailed description of various embodiments in connection with the accompanying drawings, in which:

FIG. 5 is a schematic perspective view of an illustrative cage engaging a spacer of an intervertebral implant according to an aspect of the disclosure;

FIG. 10A is a schematic top view of an illustrative intervertebral implant according to an aspect of the disclosure;

FIG. 10B is a schematic proximal side view of the illustrative intervertebral implant depicted in FIG. 10A;

FIG. 11A is a schematic top view of an illustrative intervertebral implant according to an aspect of the disclosure;

FIG. 11B is a schematic proximal side view of the illustrative intervertebral implant depicted in FIG. 11A;

FIG. 11C is a schematic top view of the illustrative intervertebral implant depicted in FIG. 11A, where a cage is turned about ninety degrees and a locking feature extends from a spacer;

FIG. 11D is a schematic proximal side view of the illustrative intervertebral implant depicted in FIG. 11C;

FIG. 18A is a schematic a lateral side view of an illustrative intervertebral implant inserted between two vertebrae, where a cage is in an inserting position according to an aspect of the disclosure;

FIG. 18B is a schematic proximal side view of the illustrative intervertebral implant depicted in FIG. 18A;

FIG. 19A is a schematic a lateral side view of the illustrative intervertebral implant depicted in FIG. 18A, where the cage is in an inserted position according to an aspect of the disclosure; and FIG. 19B is a schematic proximal side view of the illustrative intervertebral implant depicted in FIG. 19A.

Figure 1:
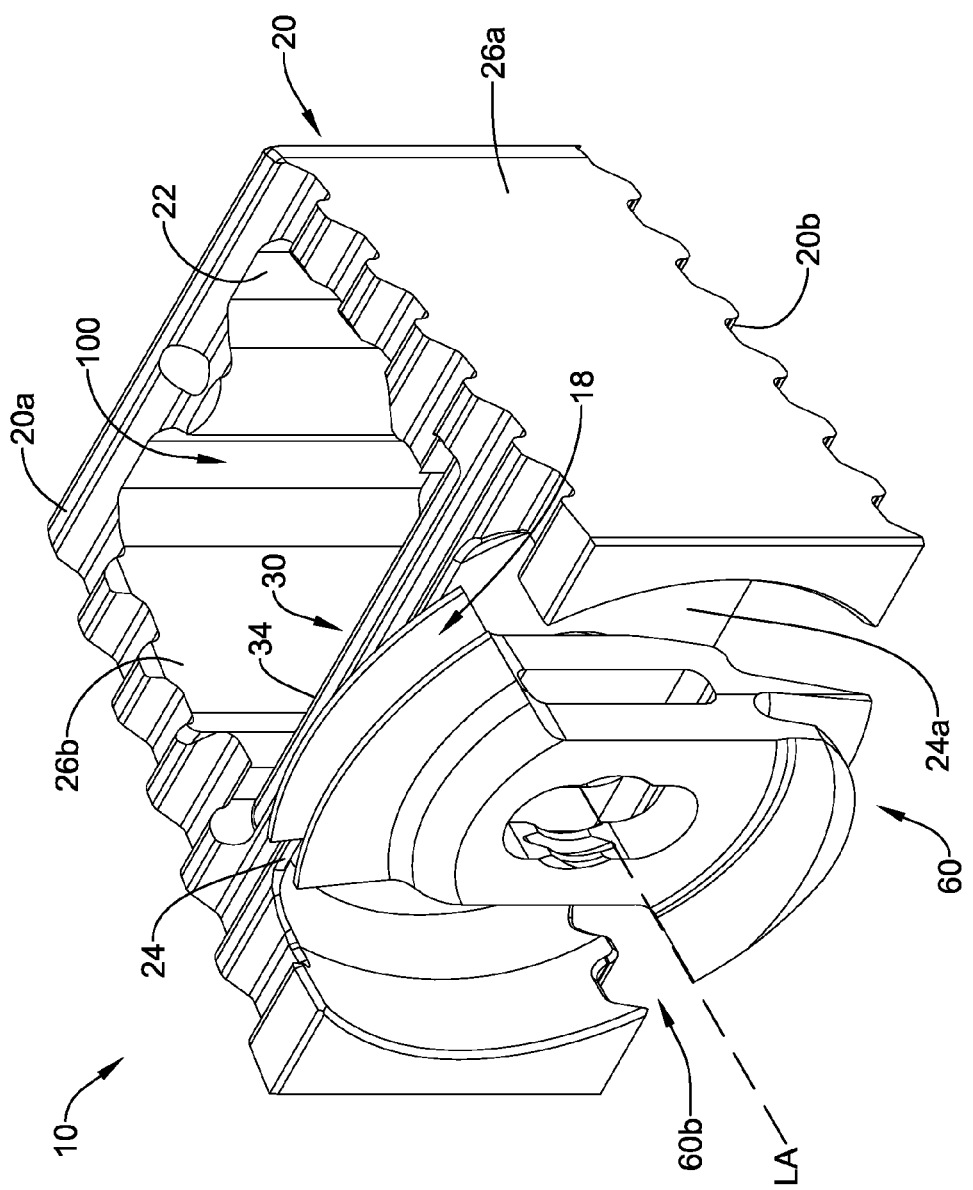
FIG. 1 is a perspective view of an intervertebral implant according to an aspect of the disclosure.

While the disclosure is amenable to various modifications and alternative forms, specifics thereof have been shown by way of example in the drawings and will be described in detail. It should be understood, however, that the intention is not to limit aspects of the claimed disclosure to the particular embodiments described. On the contrary, the intention is to cover all modifications, equivalents, and alternatives falling within the spirit and scope of the claimed disclosure.

DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

As used herein, the proximal end (i.e., trailing end) of an implant is the end that is closest to the individual or instrument inserting the implant during a medical procedure and the distal end (i.e., leading end) of an implant is the end that is farthest from the individual or instrument inserting the implant during a medical procedure.

The following detailed description should be read with reference to the drawings in which similar elements in different drawings are numbered the same. The detailed description and the drawings, which are not necessarily to scale, depict illustrative embodiments and are not intended to limit the scope of the claimed disclosure. The illustrative embodiments depicted are intended only as exemplary. Selected features of any illustrative embodiment may be incorporated into an additional embodiment unless clearly stated to the contrary.

Turning to the figures, FIGS. 1-17 depict illustrative interbody implants, such as intervertebral or spinal implants 10. Generally, implant 10 may include a spacer 20 and a cage 60. The concept of combining spacer 20 with cage 60 may facilitate providing one or more grafting spaces 100 (see e.g., FIG. 17 for more than one grafting space 100) between vertebrae and capitalize on the ability of spacer 20 to distribute the loads of the spine across vertebral endplates, while utilizing cage 60 to fixate implant 10 between vertebrae such that migration of spacer 20 is substantially prevented until fusion occurs. Although implant 10 may be suited for application to the spine through an anterior approach (e.g., to the cervical and thoracolumbar areas of the spine), implant 10 may be applied at other portions of the spine and/or body and/or modified to facilitate additional approaches or techniques (e.g., anterior oblique, lateral, etc.), as desired and as appropriate.

The spacer 20 and cage 60 concept for spinal implants 10 may include one or more of several different structures and/or concepts in which the cage 60 may or may not connect to the spacer 20. Where the cage 60 is connected to the spacer 20, one or more connection techniques may be utilized (e.g., a snap connection, a threaded connection, pre-molded connection, etc.). Alternatively, or in addition, spacer 20 may include one or more various latching and/or locking mechanisms 30 to facilitate the operation of the connected spacer 20 and cage 60 (e.g., a threaded post 48, spring loaded post 53, cam 54, etc.).

Figure 2:
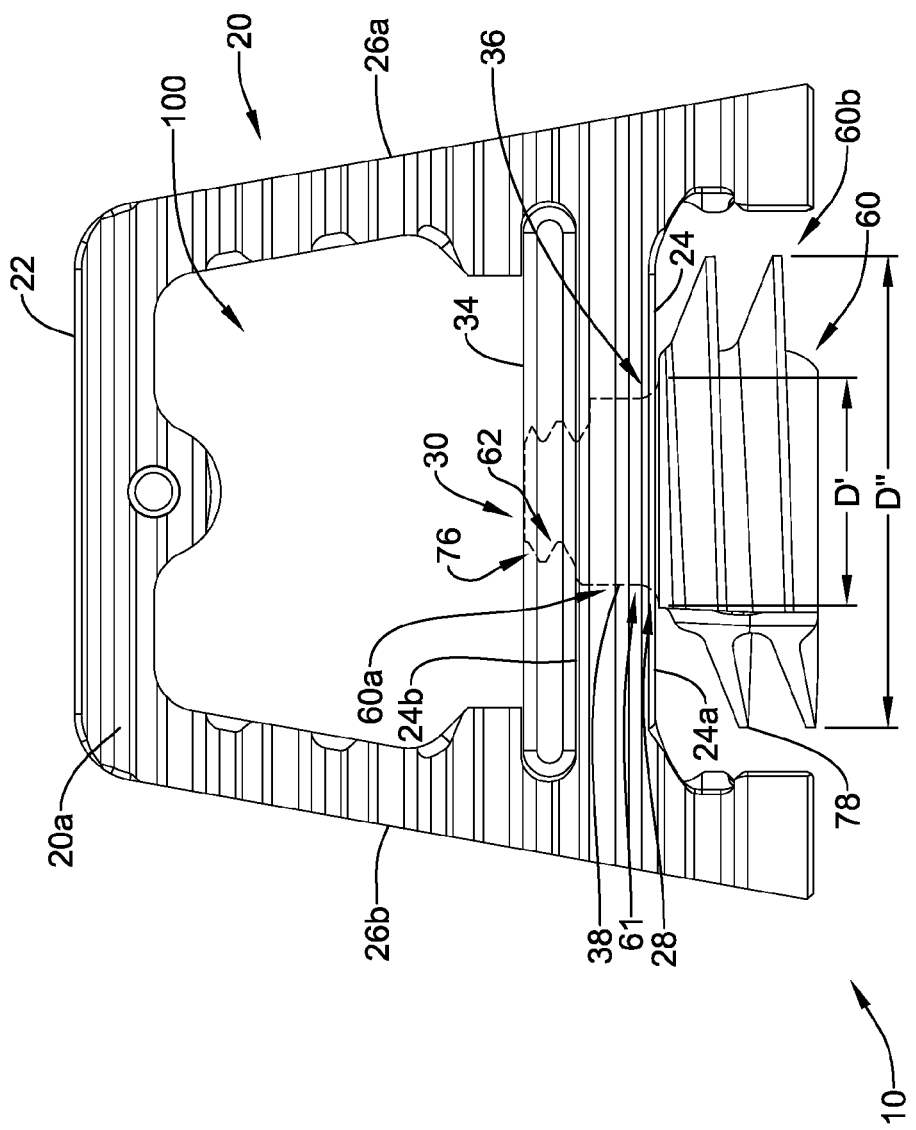
FIG. 2 is a top view of the intervertebral implant depicted in FIG. 1.
Figure 3A:
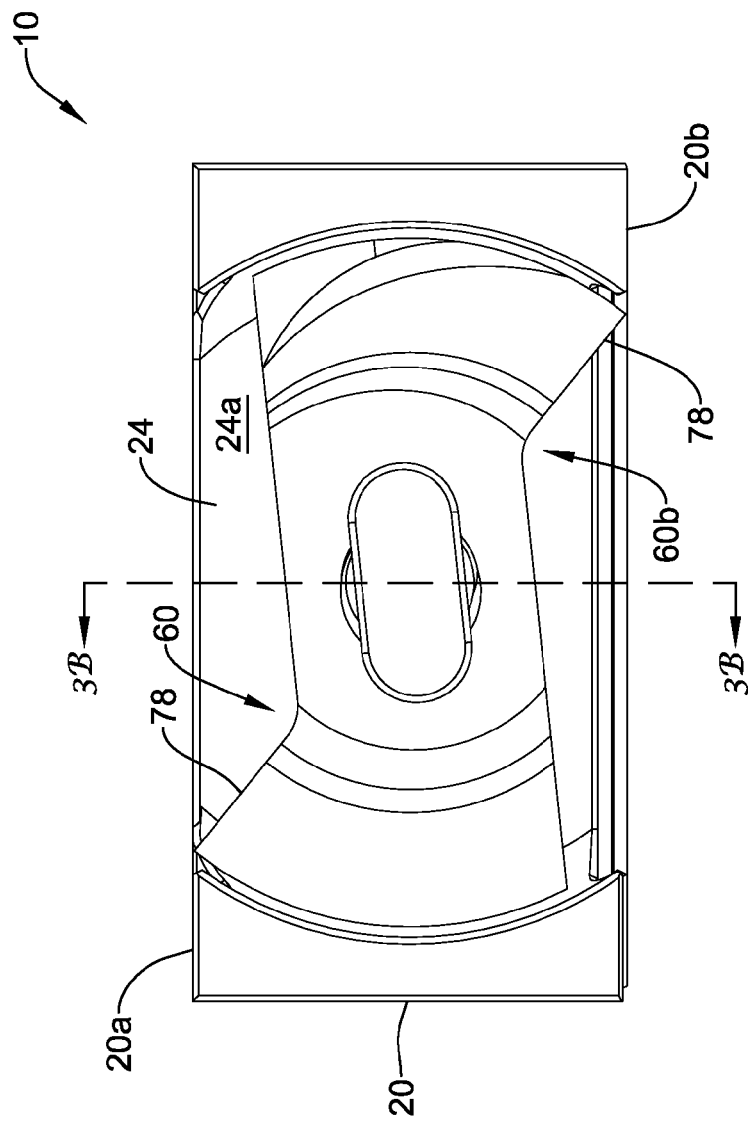
FIG. 3A is proximal side view of the intervertebral implant depicted in FIG. 1, where a cage of the intervertebral implant is in an illustrative inserting position according to an aspect of the disclosure.
Figure 3B:
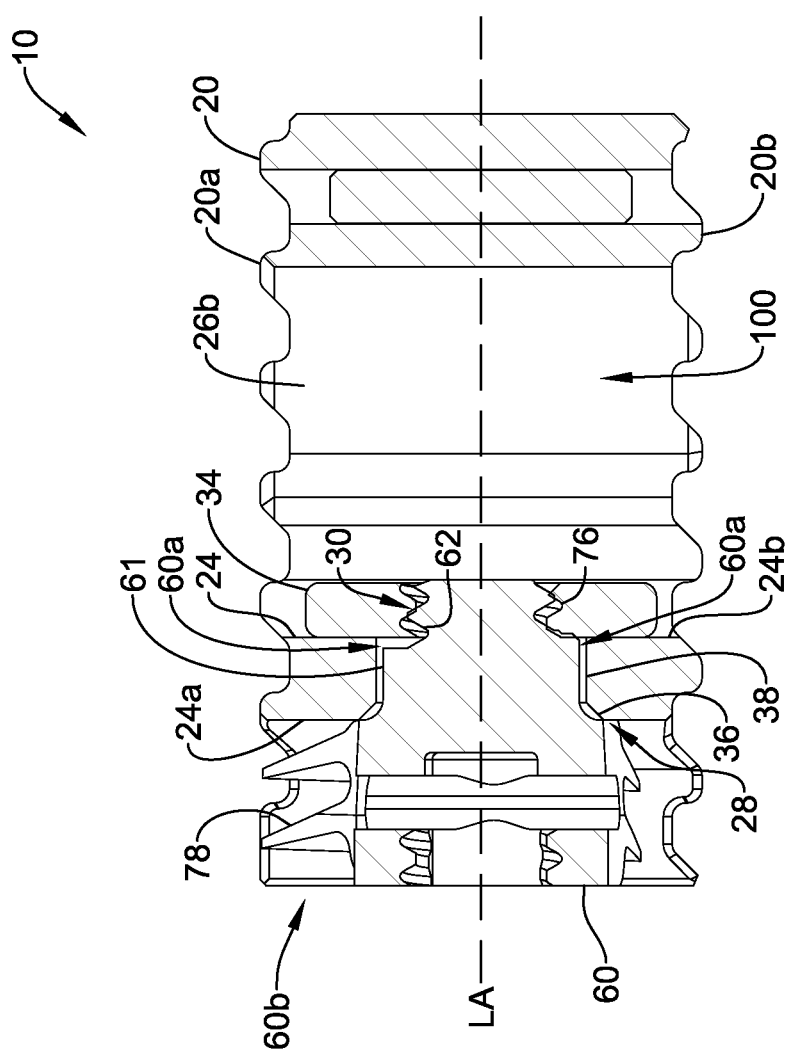
FIG. 3B is a schematic sectional view of the intervertebral implant depicted in FIG. 3A taken along line 3B-3B.
Figure 4A:
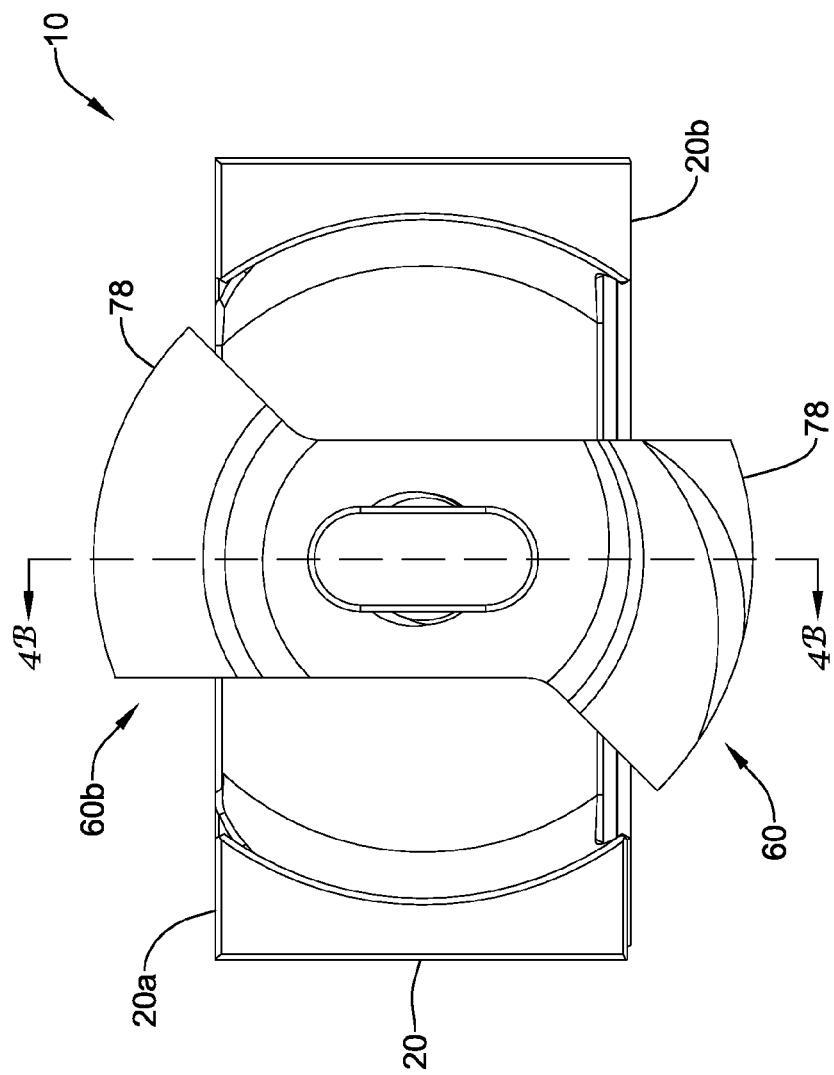
FIG. 4A is a schematic proximal side view of the intervertebral implant depicted in FIG. 1, where a cage of the intervertebral implant is in an illustrative inserted position according to an aspect of the disclosure.
Figure 4B:
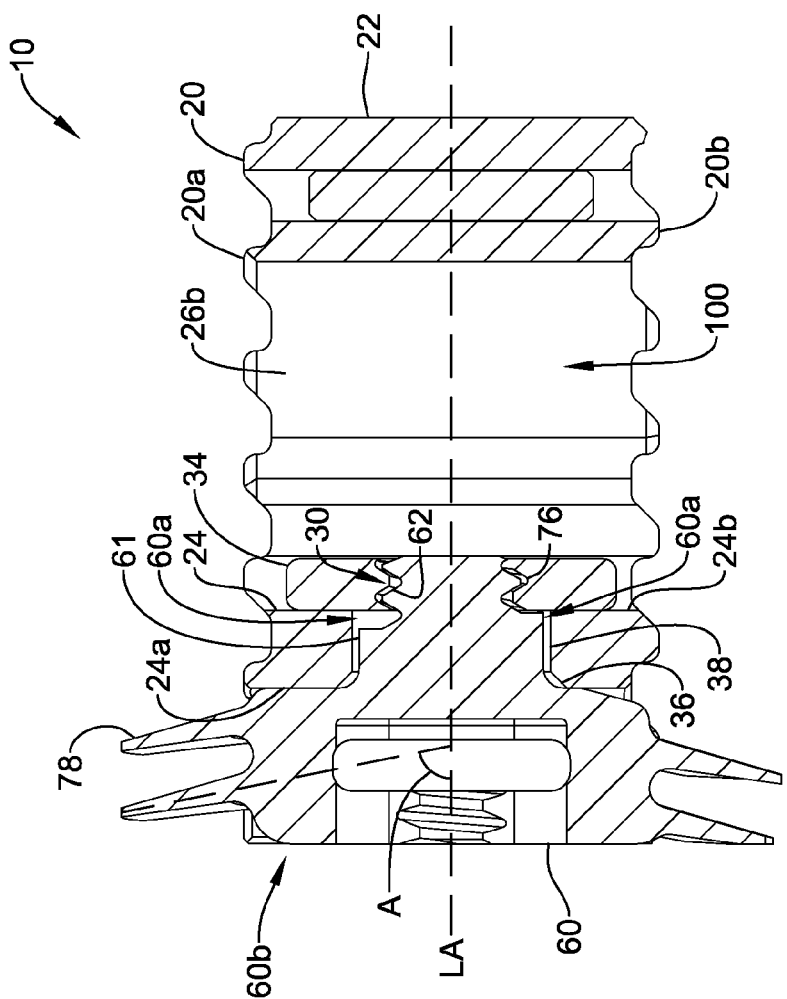
FIG. 4B is a schematic sectional view of the intervertebral implant depicted in FIG. 4A taken along line 4B-4B.

FIGS. 1-4B depict an illustrative implant 10 including a spacer 20 and cage 60, where cage 60 may include locking threads 62 positioned at a first portion or end 60a of cage 60, where the locking threads 62 may be configured to facilitate a connection between spacer 20 and cage 60. Locking threads 62 may engage spacer 20 directly and/or may engage a plate insert 34 that may be in fixed connection with spacer 20 (e.g., as seen in FIGS. 2, 3B and 4B). For example, in some embodiments, spacer 20 may be formed of a polymeric material, such as PEEK, while plate insert 34 may be formed of a metallic material, such as titanium or stainless steel. Accordingly, engagement of locking threads 62 with metal plate insert 34 may provide a more secure engagement than with a polymer material such as spacer 20. Locking threads 62 may engage spacer 20 and/or plate insert 34 in such a manner as to create a connection between cage 60 and spacer 20 (e.g., FIG. 3B), while allowing cage 60 to rotate less than 180 degrees from an inserting position to an inserted position after implant 10 has been inserted between two adjacent vertebrae to lock the cage 60 in position with respect to spacer 20 (e.g., FIG. 4B). In some instances, the cage 60 may be rotated about ninety degrees from the inserting position to the inserted position to lock the cage 60 with respect to the spacer 20 and resist further rotation of the cage 60 in either direction. For example, in some embodiments, the implant 10 may be configured such that the cage 60 is rotated about 60°, about 75°, about 80°, about 90°, about 100°, about 110°, about 120°, about 130° or about 135°, with respect to the spacer 20 to the inserted position, and thereafter resists further rotation of the cage 60 in either direction. Through rotation of cage 60 after the implant 10 has been inserted, cage 60 may engage the adjacent vertebrae with exterior (e.g., vertebrae engaging) vertebrae threads 78, where the exterior vertebrae threads 78 may optionally be self-tapping so as to engage vertebrae upon rotation.

Spacer 20 may include any structure configured to be inserted into a space between adjacent vertebrae and to maintain that space. For example, as depicted in FIGS. 1 and 2, an illustrative spacer 20 may include a distal end wall 22, a proximal end wall 24 spaced from the distal end wall 22, a first lateral wall 26a, and a second lateral wall 26b spaced from the first lateral wall 26a. In the example spacer 20, first and second lateral walls 26a, 26b may be at least partially spaced apart by proximal end wall 24 and distal end wall 22, and proximal end wall 24 and distal end wall 22 may be at least partially spaced apart by first and second lateral walls 26a, 26b, as seen in FIG. 2. In some cases, one or both of the proximal end wall 24 and the distal end wall 22 may be positioned at respective ends of the first and second lateral walls 26a, 26b. Alternatively, or in addition, one or both of the proximal end wall 24 and the distal end wall 22 may be positioned between the ends of first and second lateral walls 26a, 26b, as seen in FIGS. 1, 2, 3B and 4B (e.g., proximal end wall 24 may be positioned at a position between the ends of first and second lateral walls 26a, 26b and distal end wall 22 may be positioned at respective ends of the first and second lateral walls 26a, 26b). In some cases, spacer 20 may include an intermediate wall extending from the distal end wall 22 at least partially and/or entirely the distance to the proximal end wall 24 and/or extending from one of the lateral side walls 26a, 26b at least partially and/or entirely the distance to the other lateral side wall 26a or 26b. The walls (e.g., walls 22, 24, 26a, 26b) of spacer 20 may form one or more locations of grafting space (as seen in FIGS. 1, 2, 3B, 4B, 5, 8-15, and 17).

The walls 22, 24, 26a, and 26b of spacer 20 may include a top side 20a and a bottom side 20b of spacer 20. One or more of the top side 20a and the bottom side 20b of spacer 20 may include ridges, teeth, grooves or other structure for engaging adjacent vertebrae. The ridges or other structure may take on any form including, but not limited to, rows of ridges (e.g., FIGS. 1, 2, 3B and 4B), waffle shaped ridges (FIG. 8) and/or any other ridge design configured to engage vertebrae and facilitate stabilization of spacer 20 at a position between two vertebrae.

In some illustrative instances, proximal end wall 24 may be configured to include a receiving opening 28 configured to receive cage 60, where receiving opening 28 may extend from a first side 24a toward and, optionally, through a second side 24b, as seen in FIG. 2. Receiving opening 28 may be configured in any manner to receive cage 60 and may include receiving threads 76 and/or any other features facilitating reception of cage 60. For example, receiving opening 28 may have a substantially constant cross-section along its axial direction (FIGS. 9A-11B) or may have a cross-section that has variation along its axial direction, where the variations may include, but are not limited to, a chamfered portion 36 (e.g., FIGS. 2, 3B, 4B, 6), an intermediate portion 38 (e.g., FIGS. 2, 3B, 4B, 6), an indent portion 40 (e.g., FIG. 6), threaded portion, and/or other similar or dissimilar portions, as desired.

Illustratively, cage 60 may take on any shape and size and may include a first portion or end 60a and a second portion or end 60b. Generally, cage 60 may be solid or may be hollow, or cage 60 may be solid at select portions and hollow at other portions, as desired. The first portion 60a and the second portion 60b of cage 60 may be any shape and/or size. For example, the first portion 60a and the second portion 60b of cage 60 may be at least partially rounded or circular and first portion 60a may have a diameter less than or equal to a first diameter D' measured at or adjacent the first side 24a of proximal wall 24 and the second portion 60b may have a second diameter D", where first diameter D' may be smaller than the second diameter D" or, alternatively, the first diameter D' and the second diameter D" may have any other desired dimensions with respect to one another. As seen in FIGS. 2, 3B, 4B-7C, 9A-11, and 13-15, the first portion 60a and the second portion 60b may take on various configurations. The various configurations of the first portion 60a and the second portion 60b may be utilized as shown, used individually, and/or used with other configurations of the same or different portions or ends 60a, 60b.

The first portion 60a of cage 60 may be configured in any manner such that it is configured to interact with and/or engage receiving opening 28, as seen in FIG. 2. For example, the first portion 60a of cage 60 may be a threaded post including the locking threads 62 configured to engage receiving threads 76 in plate 34 and/or receiving opening 28, where the locking threads 62 may extend from an extension 61 of first portion 60a. The extension 61 of first portion 60a may extend from the second portion 60b of cage 60 to locking threads 62, where extension 61 may be configured to at least partially abut and/or be inserted through the chamfered portion 36 and the intermediate portion 38 of proximal wall 24 of spacer 20.

Second portion 60b may be configured in any manner such that it is configured to engage vertebrae between which implant 10 has been or is to be placed with exterior vertebrae threads 78. The exterior vertebrae threads 78 may have any shape and/or size configured to extend a diameter D". For example, exterior vertebrae threads 78 may extend entirely around a circumference substantially concentric about a longitudinal axis LA of cage 60 or may extend partially around a circumference substantially concentric about the longitudinal axis LA of cage 60.

In some instances, the exterior vertebrae threads 78 may have a reverse angle thread shape, as seen in FIGS. 3B and 4B, or the vertebrae threads 78 may take on any combination of other shapes and features, as desired. The reverse angle threads may be any threaded shape and/or direction configured to facilitate cage 60 advancing when exterior thread(s) 78 engage vertebra, but also configured to prevent cage 60 from backing out after exterior thread(s) 78 have engaged vertebrae. Illustrative reverse angle threads may include, but are not limited to, any threads that form an acute angle A in the direction of or opposite an advancing direction, where the acute angle A is with respect to the longitudinal axis LA. In other words, reverse angle threads may include upper flanks and lower flanks that angle from the longitudinal axis LA in the same direction. The inclusion of reverse angle threads may prevent the vertebral bodies superior to and inferior to the cage 60 from moving away from one another, or lifting off of the spacer 20 as the cage is screwed into the vertebral bodies, and subsequent to securement between the vertebral bodies.

Implant 10 may include a locking mechanism 30 configured to facilitate positioning cage 60 with respect to spacer 20. The locking mechanism 30 may be any object, system of objects, or any other device that may be a part of or may work with cage 60 and spacer 20 to facilitate positioning cage 60 with respect to spacer 20. Locking mechanism 30 may be configured to lock the cage 60 relative to the spacer 20 into an inserted position as the cage 60 is rotated from an inserting position in which the cage 60 is configured to pass freely into the space between adjacent vertebrae to an inserted position in which the cage 60 is configured to threadably engage the adjacent vertebrae. In some instances, the cage 60 may be rotated about ninety degrees from the inserting position to the inserted position to lock the cage 60 with respect to the spacer 20 and resist further rotation of the cage 60 in either direction. For example, in some embodiments, the implant 10 may be configured such that the cage 60 is rotated about 60°, about 75°, about 80°, about 90°, about 100°, about 110°, about 120°, about 130° or about 135°, with respect to the spacer 20 to the inserted position, and thereafter resists further rotation of the cage 60 in either direction. In some instances, the locking mechanism 30 may lock the cage 60 from movement relative to the spacer 20 upon rotation of the cage 60 less than 180 degrees, for example, substantially ninety degrees (i.e., a quarter turn) from the inserting position.

The locking mechanism 30 may include the plate insert 34 having receiving threads 76 therein, as seen in FIGS. 2, 3B and 4B, any or all portions of the receiving opening 28, the indent portion 40, the first portion 60a of cage 60, any other object and/or device, and any combination of objects and/or devices. In illustrative instances where the locking mechanism 30 includes the plate insert 34, the plate insert 34 may be a single piece of material (as seen in the Figures) or two or more pieces of material working together. As seen in FIG. 2, plate 34 may be positioned adjacent and/or may abut first side 24a of proximal end wall 24 and may be configured and positioned to facilitate locking cage 60 in place with respect to spacer 20 by mating locking threads 62 of cage 60 with receiving threads 76. Further, plate 34 may be formed integral with spacer 20 (e.g., as part or separate from proximal wall 24) and/or may be a separate object affixed relative to proximal end wall 24 or other portion of the spacer 20, as desired.

The receiving threads 76 of plate insert 34 may be formed in an interior portion of plate insert 34 (e.g., without intersecting edges of plate insert 34) or may utilize the exterior or edges of plate insert 34. In some instances, the receiving threads 76 may align with and share an axis with the receiving opening 28 of proximal end wall 24, where the receiving threads 76 and the receiving opening 28 may be concentric about the shared axis. The receiving threads 76 of the plate insert 34 may be timed with the locking threads 62 of cage 60 such that rotation of the cage 60 from the inserting position to the inserted position draws the cage 60 against the spacer 20 to lock the cage 60 into the inserted position and resists further rotation of the cage 60 in either direction.

Although the locking mechanism 30 is shown as including receiving threads 76 in insert plate 34 are shown in FIGS. 2, 3B and 4B, locking mechanism 30 may include other features configured to be utilized in combination with and/or separately from the receiving threads 76 to facilitate locking cage 60 in place with respect to spacer 20. For example, locking mechanism 30 may include, but is not limited to, one or more deflection inserts 64, 66 of cage 60 (FIGS. 5-9B), an indent portion 40 of spacer 20 (FIGS. 5-9B), a threaded post 48 (e.g., FIGS. 10A and 10B), a spring loaded post 76 (e.g., FIGS. 11A and 11B), a locking hole 50 (e.g., FIGS. 10A-11B), a spring 52 (e.g., FIGS. 11A and 11B), a cam 54 (e.g., FIG. 12), and other similar and dissimilar objects.

Figure 6:
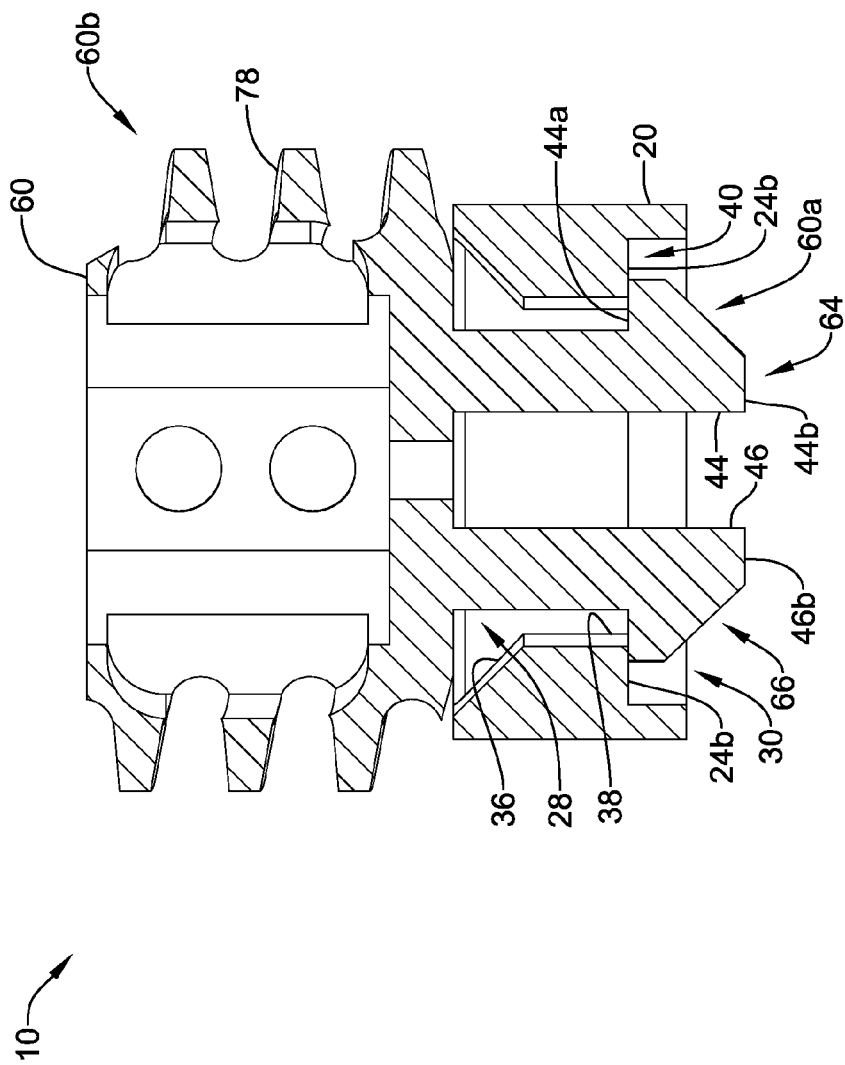
FIG. 6 is a schematic sectional view of the illustrative cage engaging the spacer of the intervertebral implant depicted in FIG. 5 taken along line 6-6, where the dotted lines of FIG. 5 have been removed.
Figure 7A:
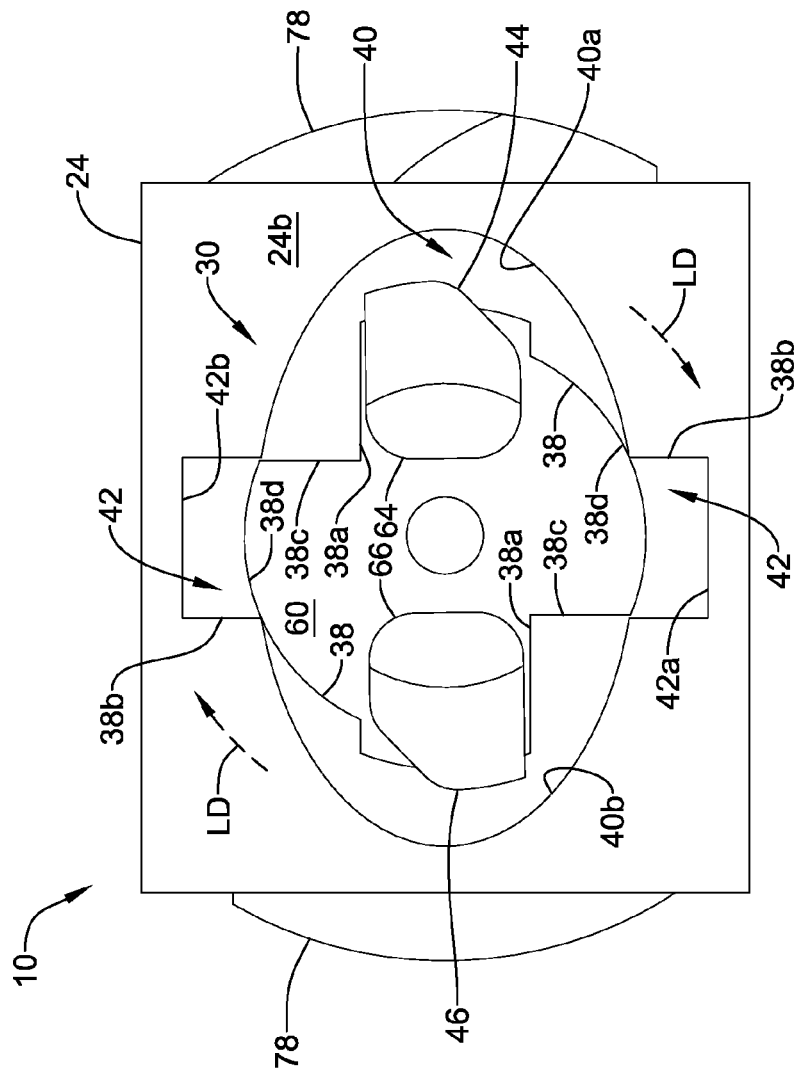
FIG. 7A is a schematic distal side view of the illustrative cage engaging the spacer of the intervertebral implant depicted in FIG. 5, where the dotted lines of FIG. 5 have been removed.
Figure 7B:
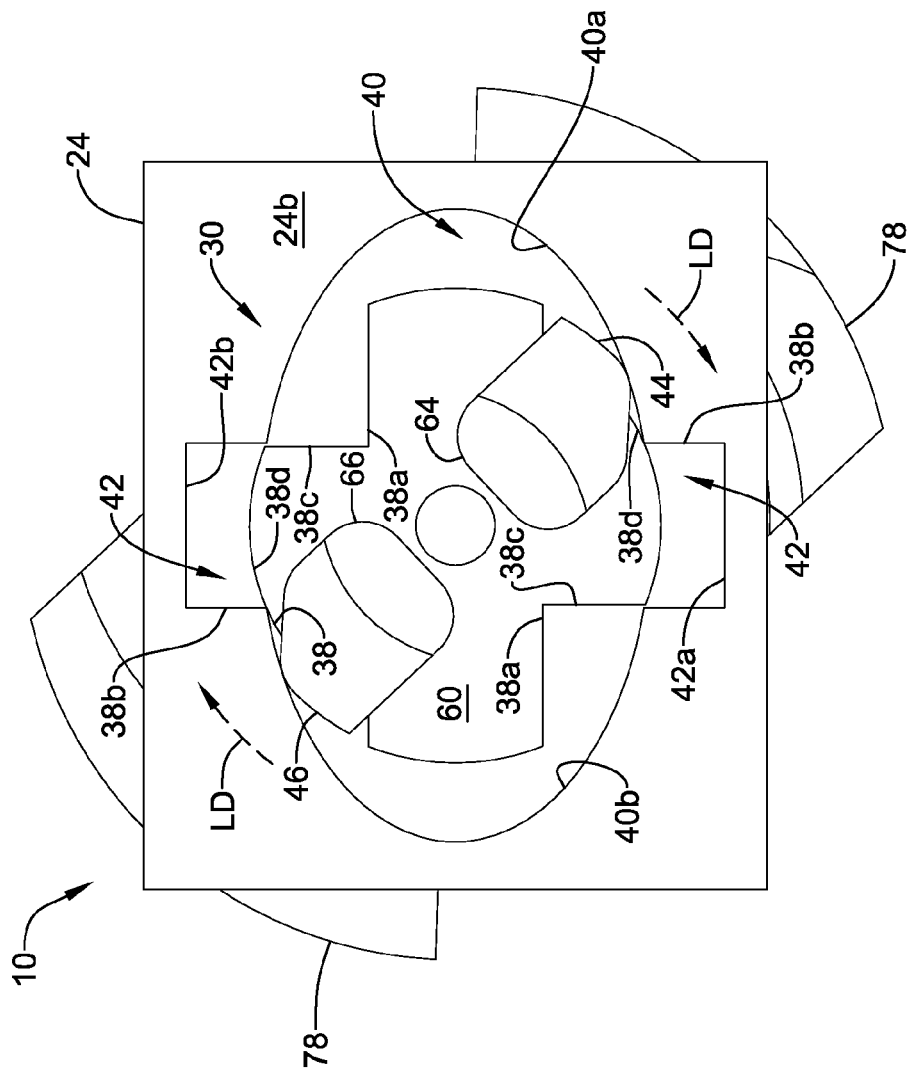
FIG. 7B is a schematic distal side view of the intervertebral implant depicted in FIG. 7A, where the intervertebral implant is in a partially inserted position according to an aspect of the disclosure.
Figure 7C:
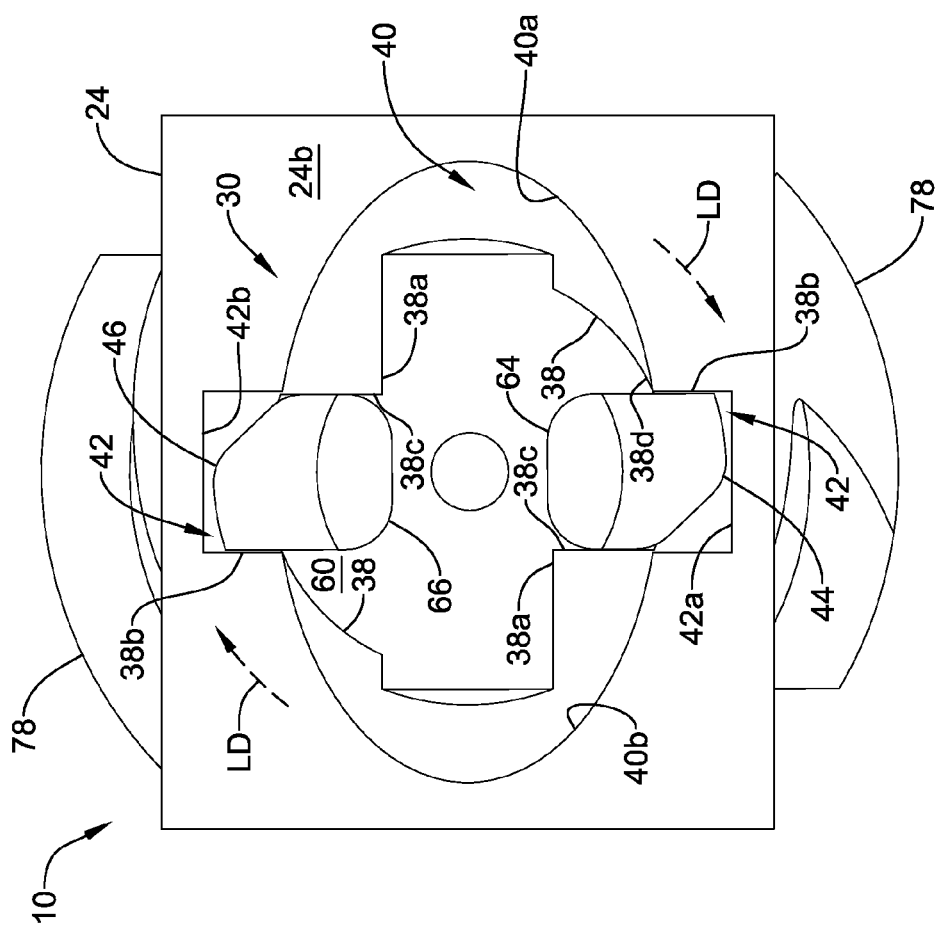
FIG. 7C is a schematic distal side view of the intervertebral implant depicted in FIG. 7A, where the intervertebral implant is in an inserted position according to an aspect of the disclosure.

Alternatively, or in addition, the locking mechanism 30 may include the intermediate portion 38 and the indent portion 40 of proximal end wall 24, where the intermediate portion 38 may extend between the second side 24a of proximal end wall 24 and/or chamfered portion 36 and indent portion 40, as depicted in FIG. 6. The indent portion 40 in combination with the intermediate portion 38 may permit movement of cage 60 in a locking direction LD, as seen in FIGS. 7A-7C. As discussed, intermediate portion 38 may have a constant cross-section configured to permit movement of the cage 60 in the locking direction LD, as seen in FIGS. 7A-7C, but not in a reverse direction or may have any other cross-section permitting movement of cage 60 in any other similar or dissimilar desired direction.

As seen in FIGS. 1-5, 7A-8 and 10-12, cage 60 may have exterior vertebrae threads 78 that extend along a portion of a circumference concentric about a longitudinal axis LA extending through cage 60. In some illustrative instances when vertebrae threads 78 extend partially around a circumference substantially concentric about longitudinal axis LA, implant 10 may be configured in an inserting position such that a substantial portion of the vertebrae threads 78 of cage 60 are positioned within spacer 20, as seen in FIGS. 3A and 3B, or within a footprint of spacer 20. In some cases, once the implant 10 has been inserted into a spinal column, or at another time, implant 10 may be configured in an inserted position such that a substantial portion of the vertebrae threads 78 of cage 60 are positioned outside of spacer 20, as seen in FIGS. 4A and 4B.

FIGS. 5-7C depict an implant 10 including spacer 20 and cage 60, where a locking mechanism 30 includes indent portions 40 and lock portions 42 of spacer 20 and one or more deflection inserts (e.g., a first deflection insert 64 and a second deflection insert 66) having one or more feet (e.g., first and second feet 44, 46). In some cases, cage 60 may be inserted into spacer 20 through a force fit. The feet 44, 46 may be at least partially tapered to facilitate the force fit or may be at least partially tapered for any other reason. In these cases and others, the first and second deflection inserts 64, 66 of the first portion or end 60a of cage 60 may be pressed against chamfered portion 36 in receiving opening 28 of spacer 20. To facilitate such an insertion technique and for other reasons, the first and second feet 44, 46 and/or at least a portion of the first and second deflection inserts 64, 66 may be configured to deflect towards one another as cage 60 is pressed into and/or through the intermediate portion 38 of the proximal end wall 24. Once the first and second feet 44, 46 have been inserted through the intermediate portion 38 of the proximal end wall 24, the first and second deflection inserts 64, 66 may be configured to revert or substantially revert to their original position, as seen in FIGS. 5 and 6.

Once feet 44, 46 having first sides or ends 44a, 46a and second sides or ends 44b, 46b have passed through receiving opening 28 of spacer 20, first sides 44a, 46a of feet 44, 46, respectively, may be configured to catch on and/or abut second side 24b of proximal end wall 24, as seen in FIG. 6. In some cases, first sides 44a, 46a of feet 44, 46 may be positioned adjacent second side 24b of proximal end wall 24 at an indent portion 40 of the proximal end wall. The intermediate portion 38 of proximal end wall 24 may have a diameter proportioned such that the first and second deflection inserts 64, 66 may revert to their natural position once the first and second feet 44, 46 have passed through the proximal end wall 24 and are positioned adjacent the second side 24b of the proximal end wall 24. In some cases, the intermediate portion 38 may have a generally circular or ovular cross-section and/or the intermediate portion 38 may have an irregular shaped cross-section that only permits movement of cage 60 in a locking direction LD (see e.g., FIGS. 7A-7C).

As seen in FIGS. 7A-7C, cage 60 may connect to spacer 20 and may be positioned in the inserting position, such that vertebrae threads 78 are positioned substantially within the spacer 20 or within a footprint of the spacer 20. From the inserting position, intermediate portion 38 of proximal end wall 24 may permit movement of cage 60 in a locking direction LD and may permit movement only in the locking direction LD to approximately ninety degrees from zero degrees at the inserting position, or another rotational amount less than 180 degrees from zero degrees. The intermediate portion 38 may be configured in any manner to facilitate rotational movement of the cage 60 in the locking direction less than 180 degrees. For example, the intermediate portion 38 may have a reverse stop ledge 38a for each deflection insert 64, 66, a catch ledge 38b for each deflection insert 64, 66, a forward stop ledge 38c for each deflection insert 64, 66, with a rounded portion 38d for guiding each of the first and second deflection inserts 64, 66, as seen in FIGS. 7A-7C. The rounded portion 38d may extend for any desired arc between the reverse stop ledge 38a and the forward stop ledge 38c. The reverse stop ledge 38a, the catch ledge 38b, the forward stop ledge 38c, and the rounded portion 38d may extend at least partially the entire length of the intermediate portion 38.

The second side 24b of proximal end wall 24 may include an indent portion 40 as part of the locking mechanism 30. The indent portion 40 may include a first arcuate portion 40a, a second arcuate portion 40b, a first lock portion 42a, and a second lock portion 42b, where the first and second arcuate portions 40a, 40b may be separated by the first and second lock portions 42a, 42b. The first and second arcuate portions 40a, 40b may take on any shape or configuration allowing the first and second feet 44, 46 to rotate in the locking direction LD as cage 60 rotates. For example, the first and second arcuate portions 40a, 40b may have an ovular arcuate shape, as seen in FIGS. 7A-7C, or the first and second arcuate portions 40a, 40b may take on any other shape or configuration, as desired. The first and second locking portion 42a, 42b may have any shape or configuration capable of containing and preventing forward or backward movement of first and second feet 44, 46. For example, first and second locking portions 42a, 42b may be configured to have three sides, where two sides are substantially parallel to one another and a third wall connects the parallel walls and may be substantially perpendicular to the parallel walls, as seen in FIGS. 7A-7C, or first and second locking portions 42a, 42b may take on any other shape or configuration, as desired.

As discussed, FIG. 7A depicts a partial view of implant 10 in an inserting position, where the vertebrae threads 78 of cage 60 may be positioned substantially within the spacer 20. FIG. 7B depicts a partial view of implant 10 in a mid-rotation position, where the cage 60 has been rotated in the locking direction LD to a position between the inserting position and the inserted position. In the mid-rotation position, the first and second feet 44, 46 may begin to engage the first and second arcuate portions 40a, 40b, respectively, which may cause the deflection inserts 64, 66 to deflect towards one another. Optionally, the deflection inserts 64, 66 may deflect towards one another during the rotation to prevent the first and second deflection inserts 64, 66 from engaging respective catch ledges 38b, to create space between intermediate portion 38 and the first and second deflection inserts 64, 66 and/or to prevent, create or facilitate any other desirable feature or operation. FIG. 7C depicts a partial view of implant 10 in an inserted position, where the cage 60 has been rotated substantially ninety degrees in the locking direction LD from the inserting position to the inserted position and the vertebrae threads 78 are positioned substantially outside of spacer 20 or substantially outside of a footprint of the spacer 20. In the inserted position, the cage 60 may be prevented from moving in a rotational direction by the locking mechanism 30 due to the first and second feet 44, 46 engaging the first and second lock portions 42a, 42b, respectively. In addition, once the cage 60 has been rotated to the inserted position, the first and second deflection inserts 64, 66 may abut or be adjacent to the forward stop ledge 38c, which may further stabilize the cage 60 while it is in the inserted position. Accordingly, the locking mechanism 30 may be configured such that rotation of the cage 60 less than 180 degrees, for example substantially ninety degrees, from the inserting position to the inserted position locks the cage 60 into the inserted position and resists further rotation of the cage 60 in either direction.

Figure 8:
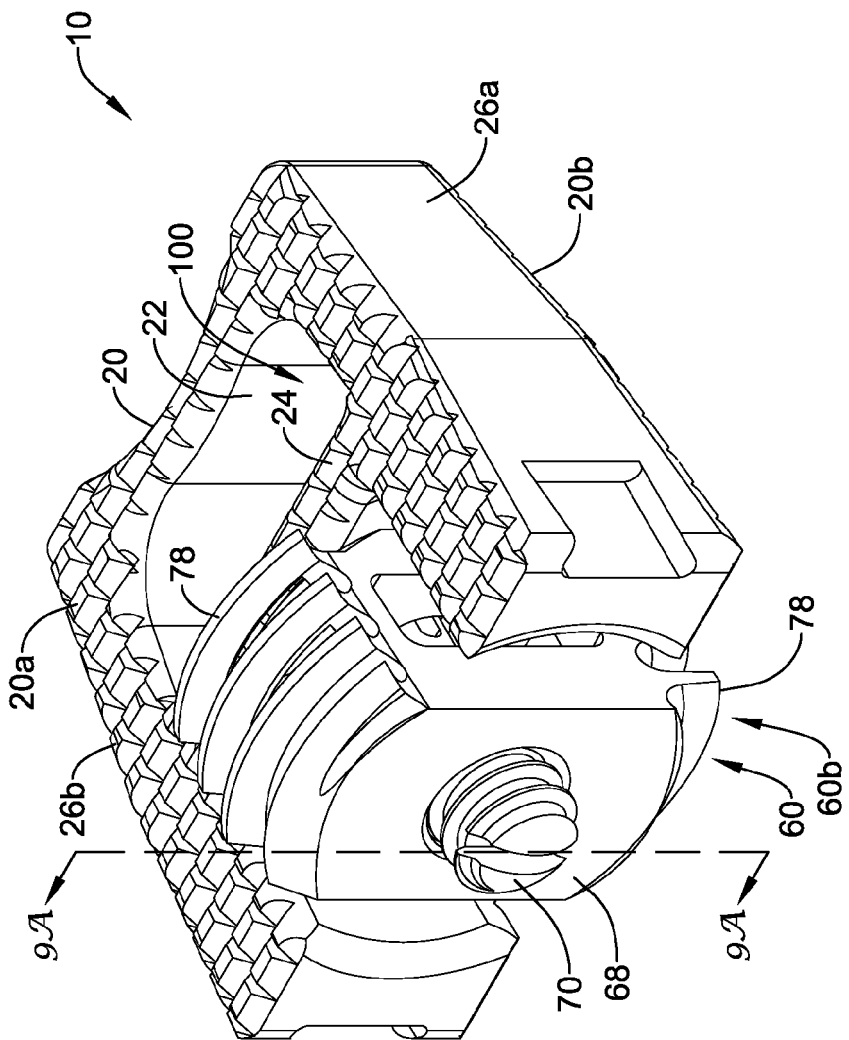
FIG. 8 is a schematic perspective view of an illustrative intervertebral implant according to an aspect of the disclosure.
Figure 9A:
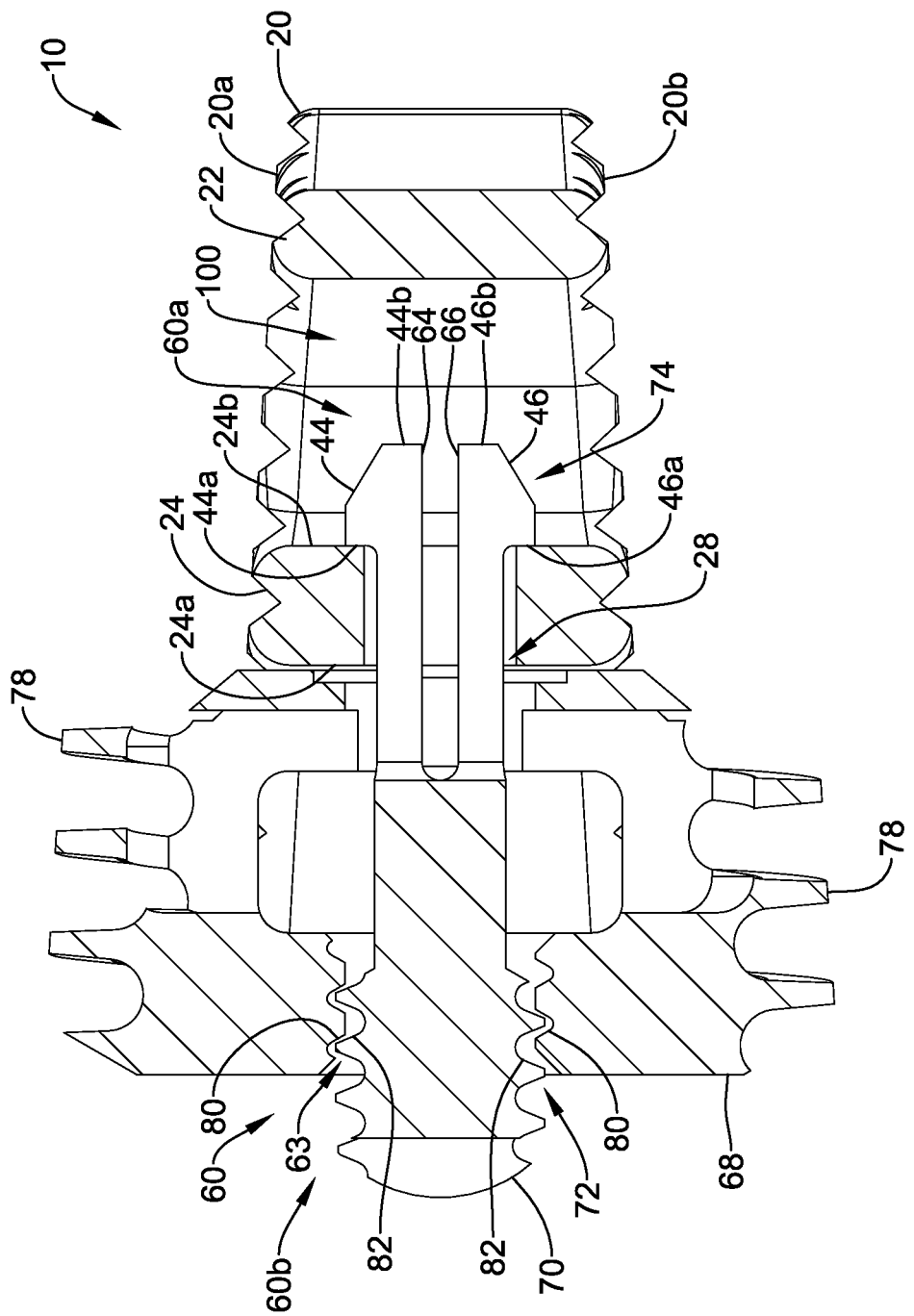
FIG. 9A is a schematic sectional view of the illustrative intervertebral implant depicted in FIG. 8 taken along line 9A-9A, where a cage is spaced from the spacer.
Figure 9B:
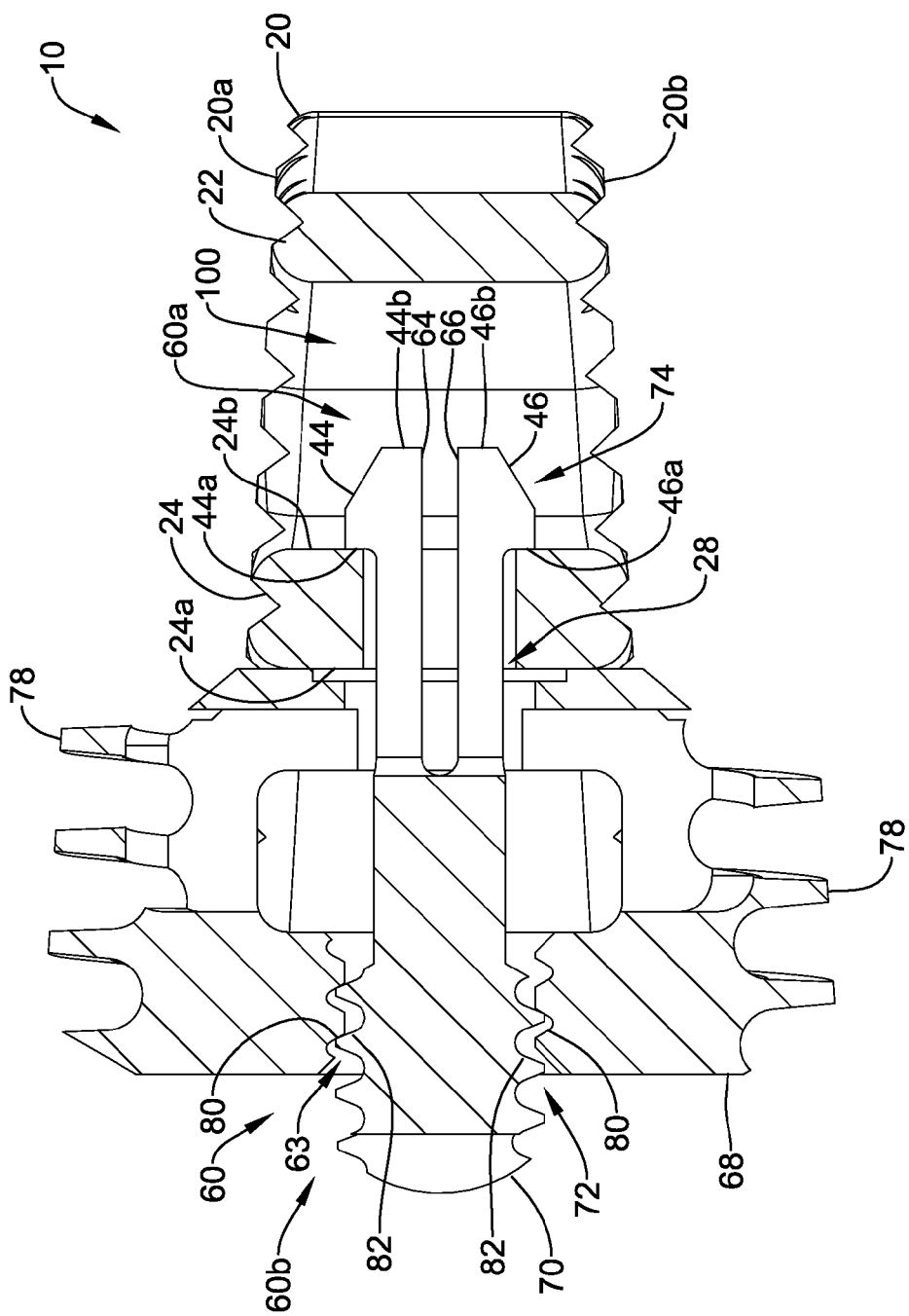
FIG. 9B is a schematic sectional view of the illustrative intervertebral implant depicted in FIG. 8 taken along line 9A-9A, where the cage is abutting the spacer.

In some illustrative instances, the cage 60 may connect with the spacer 20 through a locking member 70, as shown in FIGS. 8-9B. The locking member 70 may be configured to extend through and connect to an engaging member 68 of cage 60. The locking member 70 of cage 60 may include a locking end 72 at the first end 60a of cage 60 and a driven end 74 at a second end 60b of cage 60, as depicted in FIGS. 9A and 9B, where locking end 72 may have driving threads 82 configured to engage interior threads 80 of the engaging member 68 and driven end 74 may have one or more deflection inserts (e.g., first and second deflection inserts 64, 66) having one or more feet (e.g., first and second feet 44, 46) configured to engage the second side 24b of the proximal end wall 24. In some cases, the cage 60 may include a cage opening 63, where the cage opening 63 may include the interior threads 80 and may be configured to receive locking member 70, as seen in FIGS. 9A and 9B. Locking member 70 may be inserted into and through cage opening 63 and locking member 70 may be connected to cage 60 through the driving threads 82 of locking member 70 engaging the interior threads 80 at the second end 60b of cage 60.

Locking member 70 may include the first and second deflection inserts 64, 66 and/or other deflection inserts, where the first and second deflection inserts 64, 66 include the first and second feet 44, 46, respectively. The first and second deflection inserts 64, 66 of locking member 70 may be configured substantially similar to the first and second deflection inserts discussed above with respect to FIGS. 5-7C. As such, the first and second deflection inserts 64, 66 may deflect towards one another when inserted into and through the receiving opening 28 of the proximal end wall 24 of spacer 20. Once the first and second deflection inserts 64, 66 have been inserted through the proximal end wall 24, the first and second feet 44, 46 each having a first side 44a, 46a and a second side 44b, 46b may abut the second side 24b of the proximal end wall 24 at the first sides 44a, 46a thereof.

In some instances where the cage 60 includes a locking member 70, the locking member 70 may be pre-assembled to engaging member 68, such that the driving threads 82 engage the interior threads 80 and are tightened to lock the locking member 70 in place with respect to the engaging member 68, prior to the driven end 74 being inserted into and through the receiving opening 28 of proximal end wall 24. Alternatively, the driven end 74 may be inserted through the engaging member 68 and the receiving opening 28 of proximal end wall 24, such that a first side 44a, 46a of feet 44, 46 abuts a second side 24b of the proximal end wall 24, prior to tightening an engagement between interior threads 80 and driving threads 82, as seen in FIG. 9A. FIG. 9B depicts a tightened engagement between the interior threads 80 and the driving threads 82, where the cage 60 abuts the second side 24b of the proximal end wall 24. In some cases, the driven end 74 may be partially inserted through the proximal end wall 24 when the engagement of the interior threads 80 and the driving threads 82 are tightened. The locking mechanism 30 in an implant 10, where the implant 10 includes a cage 60 having a locking member 70, may comprise the engagement between the locking member 70 and the engaging member 68 along with the engagement between the deflection inserts 64, 66 and the proximal end wall 24, and/or any other combination to features utilized for creating a connection between cage 60 and spacer 20. Once the cage 60 has been connected to spacer 20, the locking member 70 may be used to lock the cage 60 in the inserted position once the cage 60 has been rotated from the inserting position to the inserted position, such as less than 180 degrees, in some instances. For example, in some instances the cage 60 may be rotated about ninety degrees from the inserting position to the inserted position and then the locking member 70 may be used to lock the cage 60 with respect to the spacer 20 and resist further rotation of the cage 60 in either direction. For example, in some embodiments, the implant 10 may be configured such that the cage 60 is rotated about 60°, about 75°, about 80°, about 90°, about 100°, about 110°, about 120°, about 130° or about 135°, with respect to the spacer 20 to the inserted position, and thereafter the locking member 70 may resist further rotation of the cage 60 in either direction. For example, once the cage 60 is rotated to the inserted position, the locking member 70 may be rotated while holding the cage 60 stationary to press an end face of the cage 60 against an end face of the spacer 20.

Figure 10C:
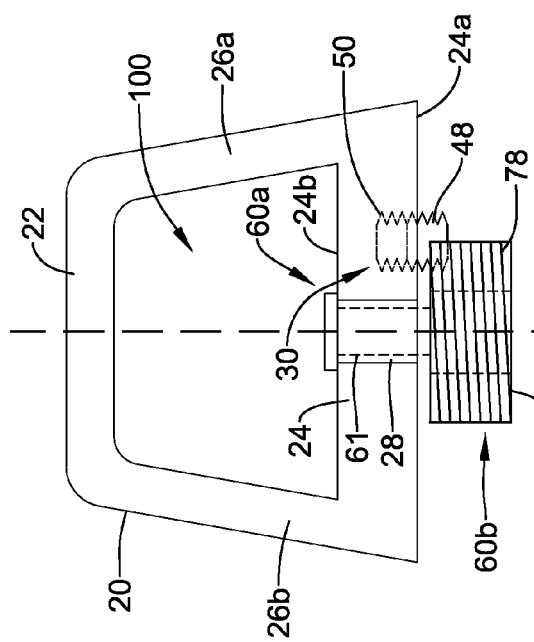
FIG. 10C is a schematic top view of the illustrative intervertebral implant depicted in FIG. 10A, where a cage is turned about ninety degrees and a locking feature extends from a spacer.
Figure 10D:
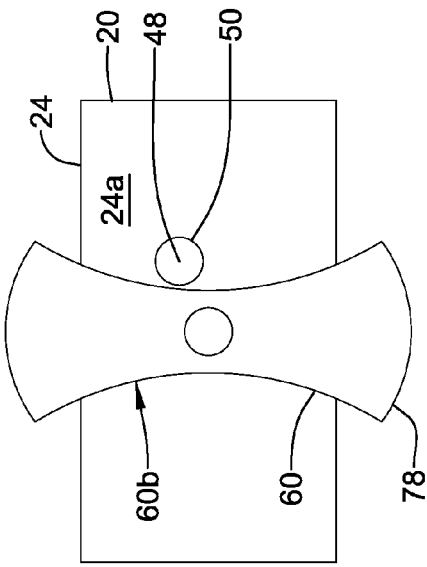
FIG. 10D is a schematic proximal side view of the illustrative intervertebral implant depicted in FIG. 10C.

In some illustrative instances where the vertebrae threads 78 of cage 60 may extend partially around a circumference substantially concentric about the longitudinal axis LA of cage 60, the locking mechanism 30 may include a locking hole 50 and a threaded post 48, as shown in FIGS. 10A-10D. Generally, the locking hole 50 may be laterally spaced from and, optionally, offset above or below the extension portion 61 of cage 60 and/or the receiving opening 28 of spacer 20 and may extend from the first side 24a of the proximal end wall 24 toward the second side 24b of proximal end wall 24. In some cases, the locking hole 50 may have threads that engage threads of the threaded post 48, where the entirety or substantially the entirety of the threaded post 48 may be positioned within locking hole 50 such that threaded post 48 may be substantially flush or flush with the first side 24a of the proximal end wall 24, as shown in FIG. 10A.

In operation, when the locking mechanism 30 of implant 10 includes the locking hole 50 and the threaded post 48, the threaded post 48 may be positioned within locking hole 50 such that the second end 60b of cage 60 may be positioned in the inserting position, as seen in FIGS. 10A and 10B. After the cage 60 of implant 10 has been rotated or moved to the inserted position, threaded post 48 may be at least partially backed out of the locking hole 50 to be positioned in a locking position. A backed out threaded post 48 may be positioned and configured to prevent rotational movement of the cage 60 in at least the direction of the threaded post 48 with respect to the extension portion 61 of cage 60.

In some illustrative instances where the vertebrae threads 78 of cage 60 may extend partially around a circumference substantially concentric about the longitudinal axis of cage 60, the locking mechanism 30 may include a locking hole 50 and a spring loaded post 53, as shown in FIGS. 11A-11D. Generally, as discussed above, locking hole 50 may be laterally spaced from and, optionally, offset above or below extension portion 61 of cage 60 and/or receiving opening 28 and may extend from the first side 24a of the proximal end wall 24 toward the second side 24b. The locking hole 50 may have any shape, size and configuration. For example, the locking hole 50 may have a first portion 50a with a first diameter and a second portion 50b with a second diameter, where the second diameter is equal to or greater than the first diameter, as shown in FIGS. 11A and 11B. The second portion 50b of locking hole 50 may be configured to include one or more springs 52 and at least a portion of the spring loaded post 53. The spring loaded post 53 may be any shape, size and configuration. For example, the spring loaded post 53 may be T-shaped with a first portion having a diameter equal to or less than the diameter of the first portion 50a of locking hole 50 and a second portion having a diameter greater than the diameter of the first portion 50a of the locking hole 50 and smaller than or equal to the diameter of the second portion 50b of locking hole 50, such that the spring loaded pin 53 may reciprocally translate within the locking hole 50, but is unable to translate out of locking hole 50.

In operation, when the locking mechanism 30 of implant 10 includes the locking hole 50, the spring(s) 52, and the spring loaded post 53, the spring loaded post 53 may be positioned within locking hole 50 such that the second end 60b of cage 60 may be positioned in the inserting position, as seen in FIGS. 11A and 11B. When the cage 60 is positioned in the inserting position, the spring loaded post 53 may be configured to abut the second end 60a of cage 60. To facilitate the contact between the spring loaded post 53 and the second end 60a of cage 60, the spring 52 may bias the post 53 toward extending out of the locking hole 50. After the cage 60 of implant 10 has been rotated or moved to the inserted position, the spring loaded post 53 may be biased out of the locking hole 50 to be positioned in a locking position. A biased out spring loaded post 53 may be positioned and configured to prevent rotational movement of cage 60 in at least the direction of the spring loaded post 53 with respect to the extension portion 61 of cage 60.

Figure 12:
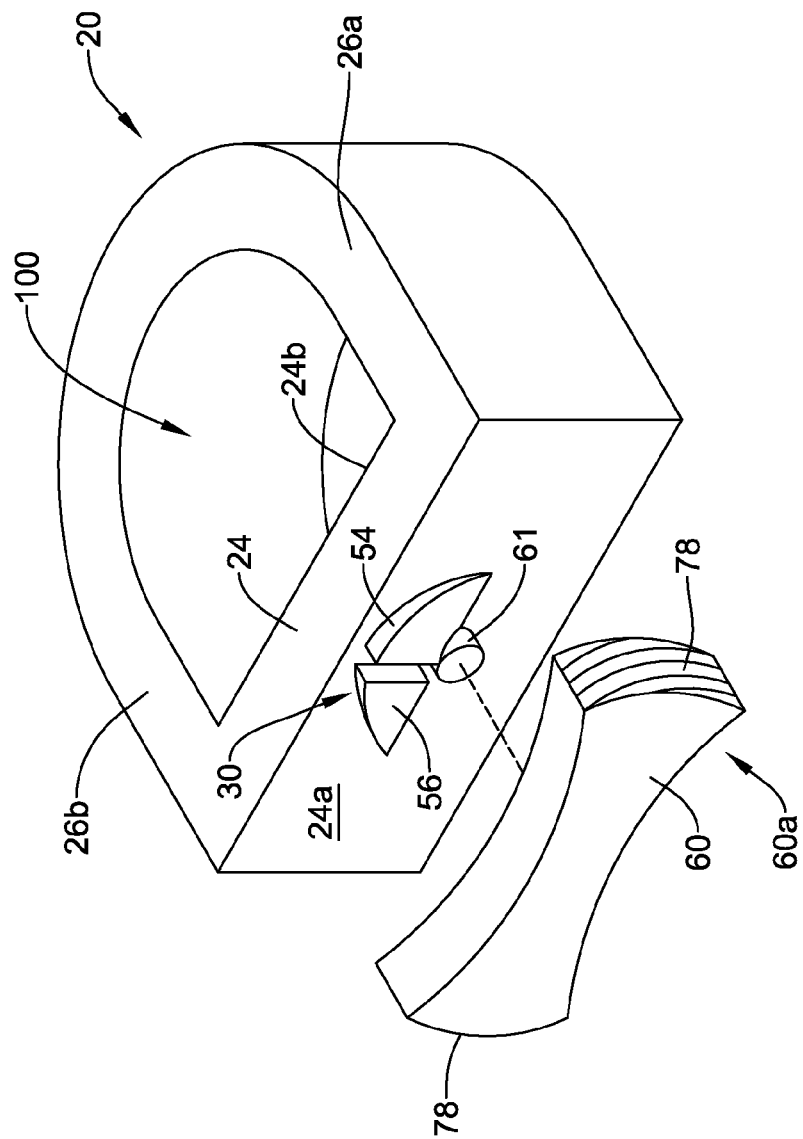
FIG. 12 is a schematic exploded perspective view of an intervertebral implant including a cam locking mechanism on a spacer according to an aspect of the disclosure.

In some illustrative instances where the vertebrae threads 78 of cage 60 may extend partially around a circumference substantially concentric about the longitudinal axis of cage 60 or in other instances, locking mechanism 30 may include a cam 54 and a cam stop 56, as shown in FIG. 12. Generally, the cam 54 and the cam stop 56 may be positioned anywhere such that when the cage 60 is rotated less than 180 degrees, for example, substantially ninety degrees, a central portion of cage 60 may be locked in a position between the cam 54 and the cam stop 56. In some cases, the cage 60 may have a protrusion, where the protrusion may be configured to slide along and/or abut cam 54 and lock the cage 60 in place between the cam 54 and the cam stop 56 when the cage 60 is rotated to the inserted or locked position. The protrusion may be a solid rigid protrusion, a ball detent system that is biased towards spacer 20 or any other protrusion configured to lock between the cam 54 and the cam stop 56 when the cage 60 is rotated from the inserting position to the inserted position. In illustrative instances where a solid rigid protrusion extends from the cage 60 and other instances, the cam 54 may be a detent that alters position in response to contact with the solid rigid protrusion.

Figure 13:
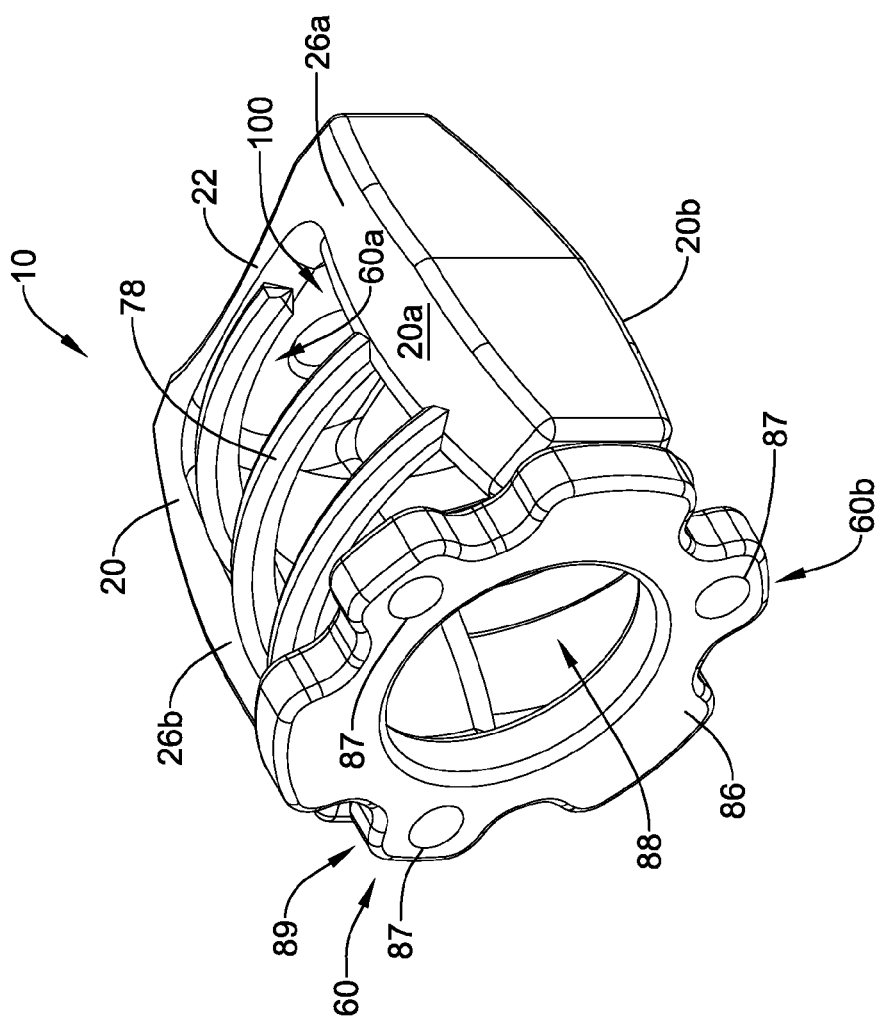
FIG. 13 is a schematic perspective view of an intervertebral implant according to an aspect of the disclosure.
Figure 14:
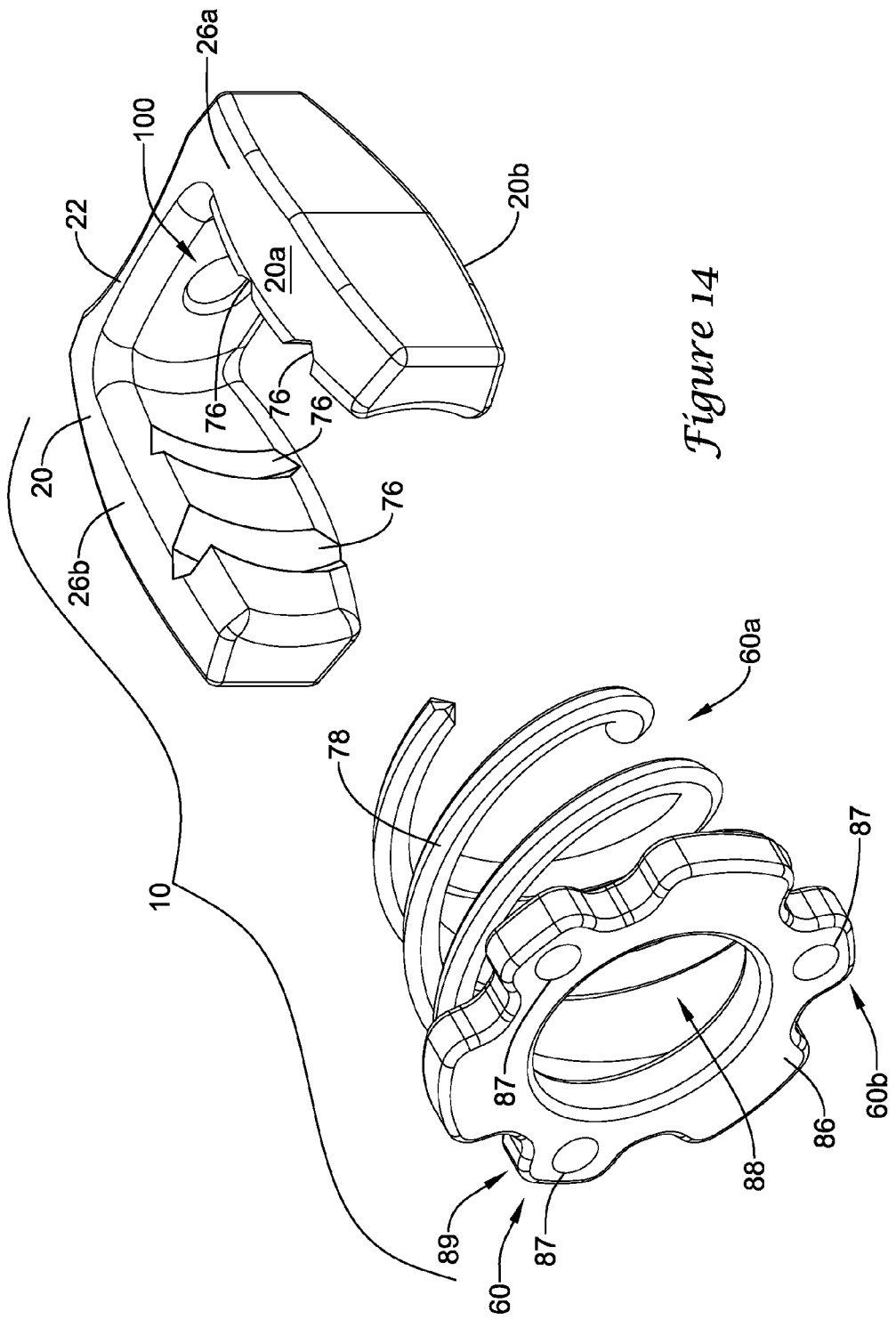
FIG. 14 is a schematic exploded perspective view of the intervertebral implant depicted in FIG. 13.

As depicted in FIGS. 13 and 14, the spacer 20 may be configured without a proximal end wall 24, such that distal end wall 22, first lateral side wall 26a, and second lateral side wall 26b substantially define grafting space 100. The cage 60 may have hollowed vertebrae threads 78 that may be configured to engage receiving threads 76 on at least interior sides of first and second lateral side walls 26a, 26b. In some cases, cage 60 may also include a handle 86 at the second end 60a, where the handle 86 may be configured to facilitate rotation of the cage 60 and the threading of the vertebrae threads 78 with the receiving threads 76. For example, the handle 86 may include a gripping surface 89 having one or more undulating surfaces or another desirable configuration, a tool grip 87 that may include one or more holes through handle 86 or another desirable configuration, and/or other mechanisms configured to facilitate rotation of the cage 60 and the threading of vertebrae threads 78 with receiving threads 76. As shown in FIGS. 13 and 14, the handle 86 may optionally include one or more handle openings 88 extending through handle 86 and into the hollow area of cage 60 defined by the vertebrae threads 78. The handle opening(s) 88 may be configured to facilitate loading a bone graft into the grafting space 100 of implant 10 after implanting the implant 10 between adjacent vertebrae.

In operation, the spacer 20 may be inserted between two adjacent vertebrae. Once the spacer 20 has been inserted between the vertebrae, the cage 60 may be placed adjacent the inserted spacer 20 and aligned so when it is rotated the vertebrae threads 78 of cage 60 are able to engage the receiving threads 76 of the spacer 20. The handle 86 may then be rotated to engage the vertebrae threads of cage 60 with the receiving threads 76 of the spacer 20 to create a tight connection between the cage 60 and the spacer 20.

Figure 15:
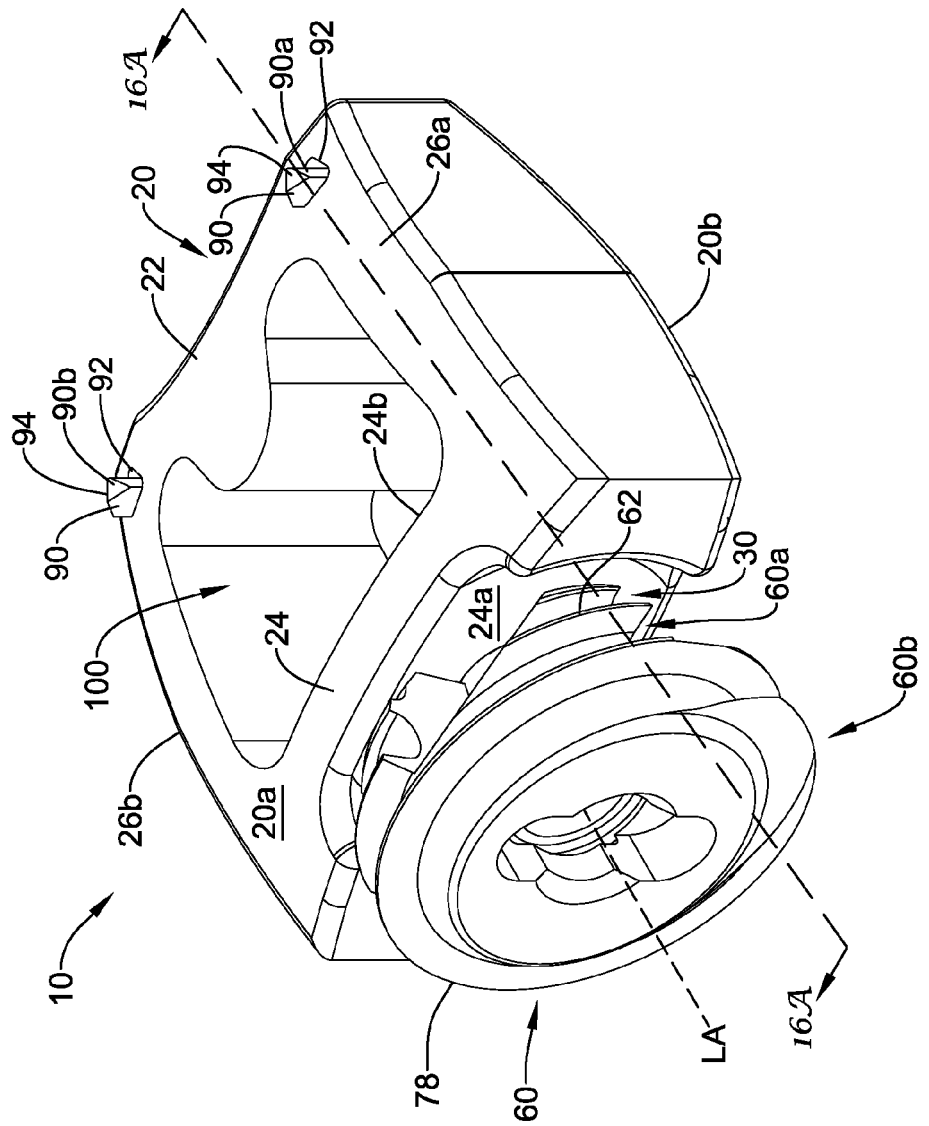
FIG. 15 is a schematic perspective view of an illustrative intervertebral implant including an engaging element according to an aspect of the disclosure.

In some instances, the implant 10 may include a spacer 20, a cage 60, locking mechanism 30, and one or more extenders (e.g., spikes 90—a first spike 90a and a second spike 90b), as shown in FIG. 15. The cage 60 may include vertebrae threads 78 at the first end 60a and locking threads 62 at the second end 60b, where the vertebrae threads 78 may extend substantially entirely around a circumference substantially concentric about the longitudinal axis LA of cage 60 (e.g., FIG. 15) or at least partially around the circumference substantially concentric about the longitudinal axis LA of cage 60. Where the vertebrae threads 78 extend substantially entirely around a circumference substantially concentric about the longitudinal axis LA, the vertebrae threads 78 may be utilized to insert the implant 10 between adjacent vertebrae. In some cases, the spacer 20 may include a proximal end wall, a distal end wall 22, a first lateral end wall 26a, and a second lateral end wall 26b, where each wall 22, 24, 26a, 26b may include a top and a bottom defined at least partially by top and bottom surfaces 20a, 20b of the spacer 20.

Figure 16A:
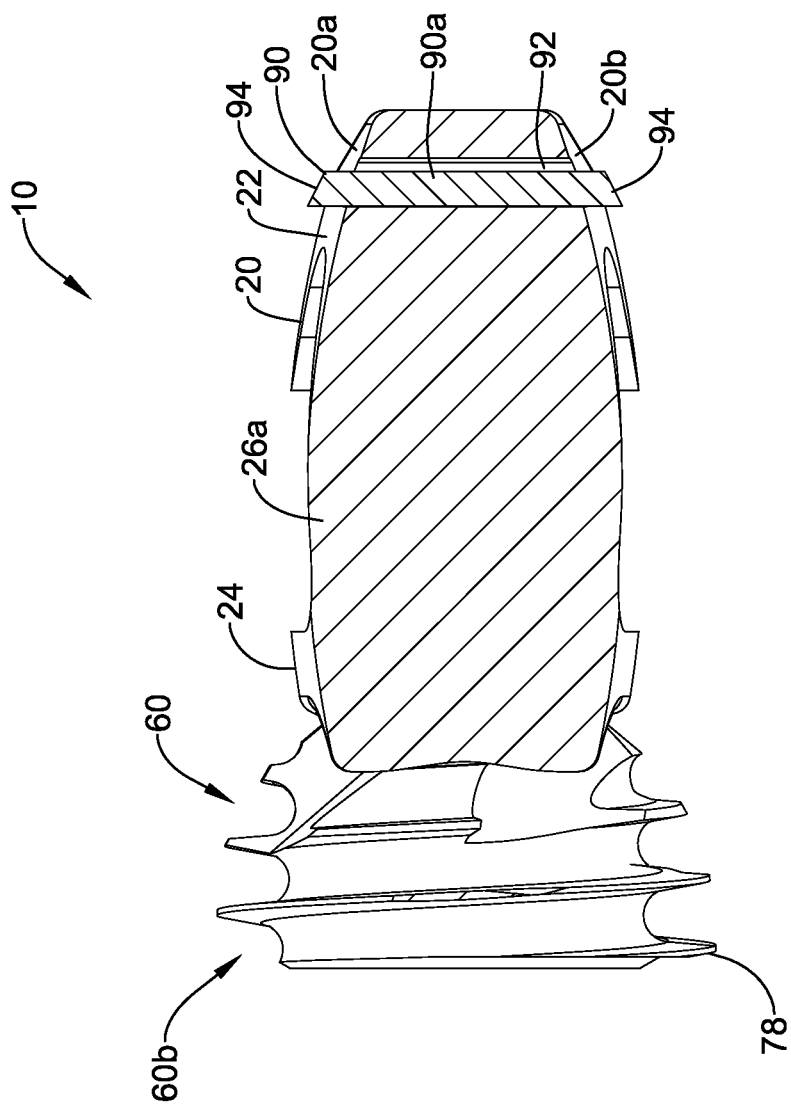
FIG. 16A is a schematic sectional view of the illustrative intervertebral implant depicted in FIG. 15 taken along line 16A-16A and having a solid engaging element.
Figure 16B:
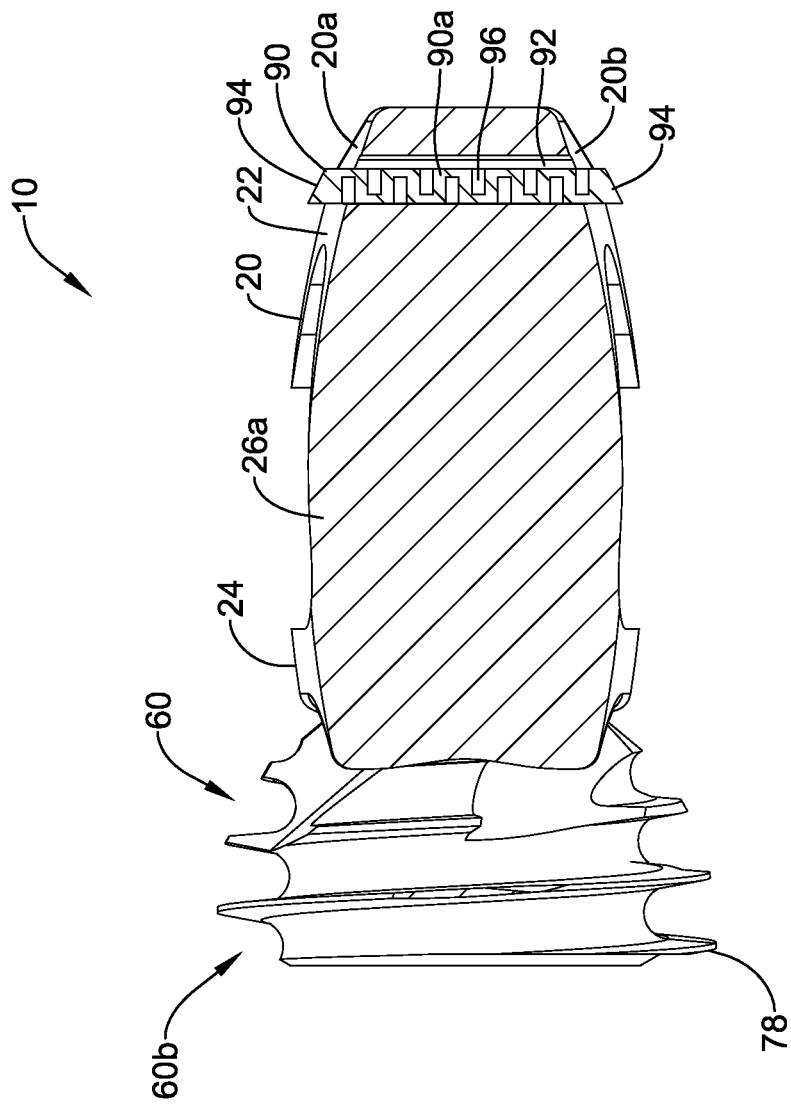
FIG. 16B is a schematic sectional view of the illustrative intervertebral implant depicted in FIG. 15 taken along line 16A-16A and having a slotted engaging element.
Figure 17:
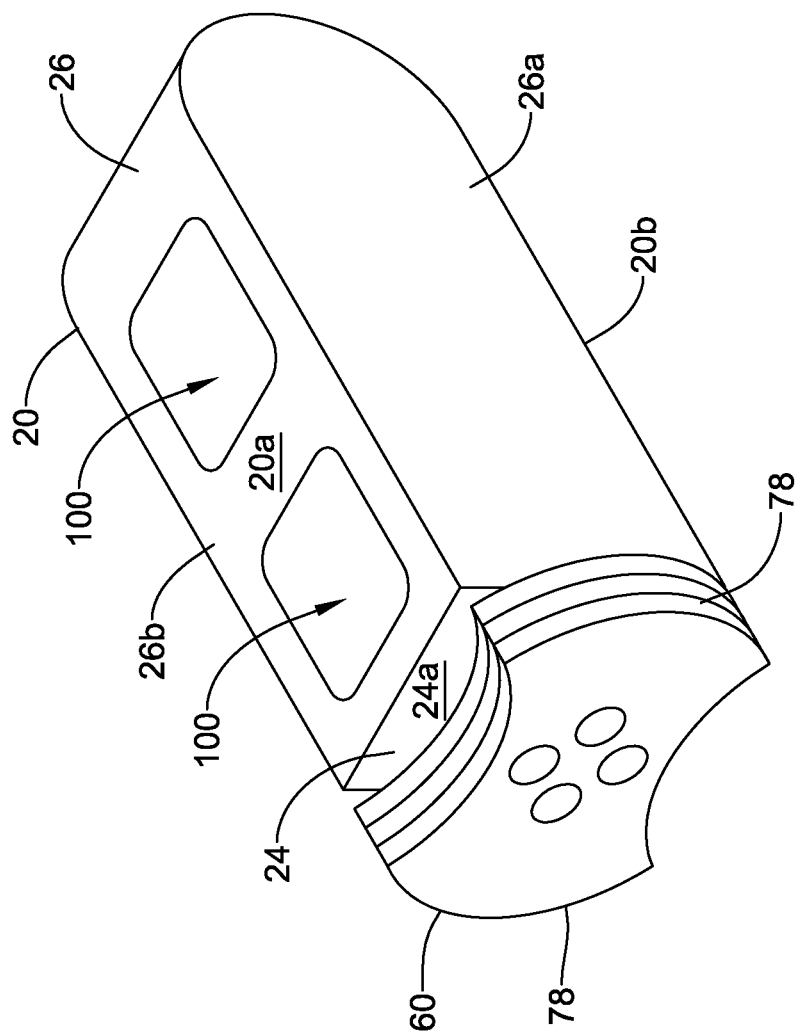
FIG. 17 is a schematic perspective view of an illustrative intervertebral implant according to an aspect of the disclosure.

The extenders or spike(s) 90 of implant 10 may be configured in any manner within or about spacer 20. The spike(s) 90 extend from or through any portion of the spacer 20 and/or the cage 60, as desired, and may be configured to provide stabilization of the implant 10 after the implant 10 has been inserted into the vertebrae column. For example, a first spike 90a may extend from the distal end wall 22 of cage 20 proximate the first lateral wall 26a and a second spike 90b may extend from the distal end wall 22 of cage 20 proximate the second lateral wall 26b. In some cases, the spike(s) 90 may extend through slots 92 and extend from one or more of the top and the bottom of the distal end wall 22 of spacer 20, as shown in FIGS. 15-16B. When the spikes 90 are positioned within the slots 92, spikes 90 may be attached to slots 92, may be at least partially loose within slots 92 and/or may have been formed as part of one of the walls 22, 24, 26a, 26b of spacer 20. As shown in FIGS. 16a and 16B, spike(s) 90 may extend all of the way through spacer 20 from the top surface 20a to the bottom surface 20b. Alternatively, or in addition, there may be one or more spikes 90 that may extend from a portion of the spacer 20 between the top and bottom surfaces 20a, 20b and through one of the top surface 20a and the bottom surface 20b.

The spike(s) 90 may be configured in any manner to extend through one or more of the top and bottom surfaces 20a, 20b of spacer 20 such that the spike(s) 90 may engage or contact adjacent vertebrae when implant 10 has been inserted between adjacent vertebrae. Each of the one or more spikes 90 may include a taper 94 that may facilitate inserting implant 10 into a position between adjacent vertebrae. Alternatively, or in addition, the spikes 90 may be configured to be compressible to facilitate the insertion of the implant 10 into the vertebral column. A spike 90 may be situated within a slot 92 to provide space for spike 90 to compress as needed to facilitate the insertion of the implant 10 in the vertebral column. A compressible spike 90 may be made of a compressible material, may have one or more slots or slits 96 configured therein (FIG. 16B) to facilitate compression of the spike 90, other compression facilitating features, and/or any combination of compression facilitating features.

The plates 34, the spacers 20, and the cages 60 discussed throughout may be made of any material. For example, the plates 34, the spacers 20, and the cages 60 may be made from metals (e.g., titanium or stainless steel), composites, polymers (e.g., polyether ether ketone (PEEK), ultra-high molecular weight polyethylene (UHMWPE), poly(methyl methacrylate) (PMMA), polyethylene terephthalate (PET), and mixtures or blends thereof), other similar or dissimilar materials, or a combination thereof, as desired.

In some illustrative instances, the implant 10 may be inserted between a first vertebrae V1 and a second vertebrae V2, as shown in FIGS. 18A-19B. FIGS. 18A and 18B show implant 10 between the first and the second vertebrae V1, V2, where implant 10 is in the inserting position and the vertebrae threads 78 extending partially around a circumference substantially concentric about the longitudinal axis LA of the cage 60 are substantially unengaged with the first and second vertebrae V1, V2. In FIGS. 19A and 19B, the implant 10 is positioned between the first and the second vertebrae V1, V2 and is in an inserted position, where the cage 60 has been rotated from the inserting position such that the vertebrae threads 78 extending partially around a circumference substantially concentric about the longitudinal axis LA of the cage 60 are engaged with the first and second vertebrae V1, V2. In some instances, the cage 60 may be rotated about ninety degrees from the inserting position to the inserted position to lock the cage 60 with respect to the spacer 20 and resist further rotation of the cage 60 in either direction. For example, in some embodiments, the implant 10 may be configured such that the cage 60 is rotated about 60°, about 75°, about 80°, about 90°, about 100°, about 110°, about 120°, about 130° or about 135°, with respect to the spacer 20 to the inserted position, and thereafter resists further rotation of the cage 60 in either direction.

Those skilled in the art will recognize that the present disclosure may be manifested in a variety of forms other than the specific embodiments described and contemplated herein. Accordingly, departure in form and detail may be made without departing from the scope and spirit of the present disclosure as described in the appended claims.

What is claimed is:
1. An intervertebral implant, comprising:
   a spacer having a distal end wall, a proximal end wall, a first lateral wall, and a second lateral wall, where the first lateral wall and the second lateral wall extend from the distal end wall to the proximal end wall, the spacer further having a top surface and a bottom surface opposite the top surface;
a locking mechanism situated at the proximal end wall;
a receiving opening extending into the proximal end wall;
a cage having a first portion and a second portion, where the first portion is configured to engage the receiving opening such that a distal end of the first portion is maintained proximal of the distal end wall and the second portion has discontinuous threads to engage vertebrae; and
wherein the first portion extends distal of the second portion such that the distal end of the first portion is distal of the discontinuous threads; and
wherein:
the cage has an axis of rotation;
the second portion of the cage extends a first distance in a first direction perpendicular to the axis of rotation;
the second portion of the cage extends a second distance in a second direction perpendicular to the axis of rotation and perpendicular to the first direction, where the second distance is greater than the first distance; and
when the first portion of the cage engages the receiving opening and the distal end of the first portion is maintained proximal of the distal end wall, the second portion of the cage is positionable between the first lateral wall, the second lateral wall, the top surface, and the bottom surface of the spacer.

2. The implant of claim 1, wherein:
the locking mechanism includes receiving threads; and
the first portion of the cage includes locking threads configured to engage the receiving threads.

3. The implant of claim 2, wherein the locking mechanism is configured such that rotation of the cage less than 180 degrees from an inserting position to an inserted position draws the cage against the spacer to lock the cage into the inserted position and resists further rotation of the cage in either a clockwise direction or a counter-clockwise direction.

4. The implant of claim 3, wherein the locking mechanism includes a plate insert abutting the proximal end wall and having the receiving threads for engaging the locking threads of the first portion of the cage.

5. The implant of claim 1, wherein the discontinuous threads include reverse angle threads to engage vertebrae, wherein the reverse angle threads include upper flanks and lower flanks that angle from the axis of rotation of the cage in the same direction.

6. The implant of claim 1, wherein the locking mechanism is configured such that rotation of the cage less than 180 degrees from an inserting position to an inserted position locks the cage into the inserted position and resists further rotation of the cage in either a clockwise direction or a counter clockwise direction.

7. The implant of claim 6, wherein:
the first portion of the cage includes a first deflection insert and a second deflection insert; and
the first deflection insert and the second deflection insert are configured to deflect toward one another when being received by the receiving opening.

8. The implant of claim 7, wherein the receiving opening is configured to facilitate deflecting the first deflection insert and the second deflection insert toward one another when being received by the receiving opening.

9. The implant of claim 8, wherein:
the proximal end wall has a first side and a second side and the receiving opening extends from the first side of the proximal end wall to the second side of the proximal end wall; and
when the first deflection insert and the second deflection insert are inserted through the receiving opening and engage the second side of the proximal end wall, the second portion of the cage is configured to abut the first side of the proximal end wall.

10. The implant of claim 9, wherein:
the receiving opening has an intermediate portion configured to permit movement of an inserted cage in a locking direction; and
the second side of the proximal end wall includes an indent portion extending from the second side of the proximal end wall toward the first side of the proximal end wall.

11. The implant of claim 10, wherein the indent portion has a first arcuate portion, a second arcuate portion, a first lock portion and a second lock portion.

12. The implant of claim 11, wherein the first arcuate portion is separated from the second arcuate portion by the first lock portion and the second lock portion.

13. The implant of claim 12, wherein:
the first deflection insert includes a first foot and the second deflection insert includes a second foot; and
the first lock portion receives the first foot when the cage is in an inserted position and the second lock portion receives the second foot when the cage is in the inserted position.

14. The implant of claim 1, wherein:
the cage includes an engaging member and a locking member, the locking member is configured to be inserted through the engaging member and rotatable therein;
the locking member having a locking end and a driving end;
the first portion of the cage comprises the locking end and the second portion of the cage comprises the driving end; and
the threads of the second portion of the cage include exterior threads.

15. The implant of claim 14, wherein:
the cage includes interior threads; and
the driving end includes driving threads configured to engage the interior threads.

16. The implant of claim 14, wherein:
the locking end includes a first deflection insert and a second deflection insert; and
the first deflection insert and the second deflection insert are configured to deflect toward one another when being received by the receiving opening.

17. The implant of claim 1, wherein:
the proximal end wall includes a first side and a second side;
the locking mechanism includes a post configured to extend from the first side of the proximal end wall when in a locking position.

18. The implant of claim 17, wherein:
the proximal end wall includes a locking hole extending from the first side of the proximal end wall toward the second side of the proximal end wall;
the locking hole is positioned at a lateral side of the receiving opening; and
the post is configured to translate within the locking hole.

19. The implant of claim 18, wherein:
the locking hole includes threads configured to engage threads located on the post, and
the threads on the post are configured to facilitate the translation of the locking mechanism within the locking hole.

20. The implant of claim 18, further comprising:
a spring positioned in the locking hole;

wherein the spring engages the locking mechanism and is compressed when the cage is in an inserting position;

wherein the spring is extended when the cage is in a inserted position.

21. The implant of claim 1, wherein:

when the first portion engages the receiving opening, the cage is rotatable from an inserting position and an inserted position;

when the cage is in the inserting position, the discontinuous threads of the second portion are positioned within the first lateral wall, the second lateral wall, the top surface, and the bottom surface of the spacer; and when the cage is in the inserted position, the discontinuous threads of the second portion are positioned above the top surface and below the bottom surface of the spacer.

22. An intervertebral implant, comprising:

a spacer having a distal end wall, a proximal end wall, a first lateral wall, and a second lateral wall, where the first lateral wall and the second lateral wall extend from the distal end wall to the proximal end wall, the spacer further having a top surface and a bottom surface opposite the top surface;

a plate insert situated on a first side of the proximal end wall, the plate insert including a threaded opening;

a receiving opening extending into the proximal end wall; and a cage having a threaded first portion and a second portion proximal of the first portion, wherein the second portion is situated on a second side of the proximal end wall opposite the first side and the threaded first portion is configured to extend through the receiving opening and threadably engage the threaded opening of the plate insert, and the second portion is configured to engage vertebrae; and wherein the second portion of the cage is positionable between the first lateral wall, the second lateral wall, the top surface, and the bottom surface when the first portion of the cage extends through the receiving opening.

23. The intervertebral implant of claim 22, wherein rotation of the cage less than 180 degrees from an inserting position to an inserted position locks the threaded first portion of the cage with respect to the threaded opening of the plate insert.

24. The intervertebral implant of claim 23, wherein rotation of the cage to the inserted position locks the cage relative to the spacer and resists further rotation of the cage in either a clockwise direction or a counter-clockwise direction.

25. The intervertebral implant of claim 22, wherein the second portion of the cage is configured to engage vertebrae above the top surface and below the bottom surface when the first portion of the cage extends through the receiving opening.

* * * * *